United States Patent [19]
Croteau et al.

[11] Patent Number: 5,876,964
[45] Date of Patent: Mar. 2, 1999

[54] GERANYL DIPHOSPHATE SYNTHASE FROM MINT

[75] Inventors: Rodney Bruce Croteau, Pullman; Mark Raymond Wildung, Colfax, both of Wash.; Charles Cullen Burke, Moscow, Id.; Jonathan Gershenzon, Jena, Germany

[73] Assignee: Washington State University Research Foundation, Pullman, Wash.

[21] Appl. No.: 951,924

[22] Filed: Oct. 16, 1997

[51] Int. Cl.$^6$ ............ C12P 21/00; C12N 15/29; C12N 15/63; C12N 5/10

[52] U.S. Cl. ........ 435/69.1; 435/252.3; 435/254.11; 435/320.1; 435/325; 435/419; 536/23.6

[58] Field of Search ................. 435/69.1, 252.3, 435/254.11, 320.1, 325, 419; 536/23.6

[56] References Cited

PUBLICATIONS

Croteau, R. and Purkett, P.T., "Geranyl Pyrophosphate Synthase: Characterization of the Enzyme and Evidence That This Chain–Length Specific Prenyltransferase is Associated with Monoterpene Biosynthesis in Sage *(Salvia officinalis)*," *Arch Biochem. Biophys.*, 271(2):524–535 (1989).

Heide, L. and Berger, U., "Partial Purification and Properties of Geranyl Pyrophosphate Synthase from *Lithospermum erythrorhizon* Cell Cultures," *Arch. Biochem Biophys.*, 273(2):331–338 (1989).

Suga, T. and Endo, T., Geranyl Diphosphate Synthase in Leaves of *Pelargonium Roseum*, *Phytochemistry*, 30(6):1757–1761 (1991).

Clastre, M. et al., "Purification and Characterization of Geranyl Diphosphate Synthase from *Vitis vinifera* L. cv Muscat de Frontignan Cell Cultures," *Plant Physiol.*, 102:205–211 (1993).

Scolnik, P.A. and Bartley, G.E., "A Table of Some Cloned Plant Genes Involved in Isoprenoid Biosynthesis," *Plant Mol. Biol. Reporter,*14(4):305–319 (1996).

*Primary Examiner*—Nancy Degen
*Assistant Examiner*—John S. Brusca
*Attorney, Agent, or Firm*—Christensen O'Connor Johnson & Kindness PLLC

[57] ABSTRACT

A cDNA encoding geranyl diphosphate synthase from peppermint has been isolated and sequenced, and the corresponding amino acid sequence has been determined. Accordingly, an isolated DNA sequence (SEQ ID No:1) is provided which codes for the expression of geranyl diphosphate synthase (SEQ ID No:2) from peppermint (*Mentha piperita*). In other aspects, replicable recombinant cloning vehicles are provided which code for geranyl diphosphate synthase or for a base sequence sufficiently complementary to at least a portion of the geranyl diphosphate synthase DNA or RNA to enable hybridization therewith (e.g., antisense geranyl diphosphate synthase RNA or fragments of complementary geranyl diphosphate synthase DNA which are useful as polymerase chain reaction primers or as probes for geranyl diphosphate synthase or related genes). In yet other aspects, modified host cells are provided that have been transformed, transfected, infected and/or injected with a recombinant cloning vehicle and/or DNA sequence encoding geranyl diphosphate synthase. Thus, systems and methods are provided for the recombinant expression of geranyl diphosphate synthase that may be used to facilitate the production, isolation and purification of significant quantities of recombinant geranyl diphosphate synthase for subsequent use, to obtain expression or enhanced expression of geranyl diphosphate synthase in plants in order to enhance the production of monoterpenoids, to produce geranyl diphosphate in cancerous cells as a precursor to monoterpenoids having anti-cancer properties or may be otherwise employed for the regulation or expression of geranyl diphosphate synthase or the production of geranyl diphosphate.

12 Claims, 2 Drawing Sheets

GERANYL DIPHOSPHATE SYNTHASE FROM MINT

This invention was supported in part by grant number DE-FG03-96ER 20212 awarded by the Department of Energy. The government has certain rights in the invention.

FIELD OF THE INVENTION

The present invention relates to nucleic acid sequences which code for geranyl diphosphate synthases, such as geranyl diphosphate synthase from *Mentha piperita*, and to vectors containing the sequences, host cells containing the sequences and methods of producing recombinant geranyl diphosphate synthases and their mutants.

BACKGROUND OF THE INVENTION

Geranyl diphosphate synthase (GPP synthase) is one of a family of enzymes called prenyl transferases that catalyze $C_5$ elongation reactions to form the linear (acyclic) precursors of the various terpenoid families. GPP synthase catalyzes the condensation of dimethylallyl diphosphate (DMAPP) and isopentenyl diphosphate (IPP) to form geranyl diphosphate (GPP) which is the immediates, $C_{10}$ acyclic precursor of the monoterpenes (Wise, M. L. and Croteau, R., in Cane, D. E., ed., "Comprehensive Natural Products Chemistry: Isoprenoids, Vol. 2", Elsevier Science, Oxford, 1997 (in press) (FIG. 1). Farnesyl diphosphate synthase (FPP synthase), a related prenyl transferase, utilizes GPP and IPP as substrates to form farnesyl diphosphates (FPP), which is the immediate, $C_{15}$ precursor of the sesquiterpenes (FIG. 1). Another prenyl transferase, geranylgeranyl diphosphate synthase (GGPP synthase), catalyzes the condensation of farnesyl diphosphate and IPP to form geranylgeranyl diphosphate (GGPP) which is the immediate $C_{20}$ precursor of the diterpene family (FIG. 1). Other types of prenyl transferases can utilize GGPP and IPP as substrates to form very long chain molecules, such as natural rubber. Poulter C. D. and Rilling, H. C., *Accts. Chem. Res.* 11: 307–313 (1978); Scolnik, P. A. and Bartley, G., *Plant Mol. Biol. Rep.* 14: 305, 307 (1996).

The basic reaction mechanism for all of these prenyl transferases is the same, and consists of three steps (see FIG. 2 in which the reaction catalyzed by geranyl diphosphate synthase is presented as illustrative of the general reaction mechanism). With reference to FIG. 2, in the first step an allylic diphosphate ester (2a) is ionized to the stable carbonium ion (2b). The carbonium ion then attacks the double bond of isopentenyl diphosphate (2c) to yield another carbonium ion (2d). In the final step of the cycle, a proton is eliminated from the newly formed carbonium ion (2d) to form a terpenoid containing a new allylic double bond (2e). In the reaction catalyzed by GPP synthase, the allylic diphosphate ester is dimethyl allyl diphosphate (FIG. 1 and FIG. 2). In the reactions catalyzed by FPP synthase and GGPP synthase the allylic diphosphate ester is geranyl diphosphate and farnesyl diphosphate, respectively (FIG. 1).

Unlike FPP synthase and GGPP synthase, which produce GPP as an intermediate and which are nearly ubiquitous (Ogura, K. and Koyama, T., in Ogura, K. and Sankawa, U., eds., "Dynamic Aspects of Natural Products Chemistry" Kodansha/Harwood Academic Publishers, Tokyo, pp. 1–23, 1997), geranyl diphosphate synthase is largely restricted to plant species that produce abundant quantities of monoterpenes. Because both FPP synthase and GGPP synthase produce only negligible levels of GPP as a free intermediate on route to FPP and GGPP (Ogura, K. and Koyama, T., supra), it is geranyl diphosphate synthase that provides the crucial link between primary metabolism and monoterpene biosynthesis and that serves as the essential driver of monoterpene biosynthesis (Wise, M. L. and Croteau, R., supra).

Any attempt, therefore, to exploit recombinant methods to increase the yield of monoterpene-producing (essential oil) species, or to genetically engineer the monoterpene biosynthetic pathway into any non-producing species (e.g., field crops, fruit-bearing plant species and animals) requires access to a geranyl diphosphate synthase gene or cDNA clone. Co-expression of geranyl diphosphate synthase along geranylgeranyl diphosphate (GGPP) which is the immediate $C_{20}$ precursor of the with a selected monoterpene synthase, such as (−)-limonene synthase (Colby et al., *J. Biol. Chem.* 268:23016–23024, 1993), and any subsequent pathway enzymes, should allow production of the corresponding monoterpene product(s) from simple carbon substrates, such as glucose, in any living organism.

Monoterpenes are utilized as flavoring agents in food products, and as scents in perfumes (Arctander, S., in *Perfume and Flavor Materials of Natural Origin*, Arctander Publications, Elizabeth, N.J.; Bedoukian, P. Z. in *Perfumery and Flavoring Materials*, 4th edition, Allured Publications, Wheaton, Ill., 1995; Allured, S., in *Flavor and Fragrance Materials*, Allured Publications, Wheaton, Ill., 1997. Monoterpenes are also used as intermediates in various industrial processes. Dawson, F. A., in *The Amazing Terpenes*, Naval Stores Rev., Mar./Apr., 6–12, 1994. Monoterpenes are also implicated in the natural defense systems of plants against pests and pathogens. Francke, W. in Muller, P. M. and Lamparsky, D., eds., *Perfumes: Art, Science and Technology*, Elsevier Applied Science, New York, N.Y., 61–99, 1991; Harborne, J. B., in Harborne, J. B. and Tomas-Barberan, F. A., eds., Ecological Chemistry and Biochemistry of Plant Terpenoids, Clarendon Press, Oxford, 399–426, 1991; Gershenzon, J and Croteau, R in Rosenthal, G. A. and Berenbaum, M. R., eds., Herbivores: Their Interactions with Secondary Plant Metabolites, Academic Press, San Diego, 168–220, 1991.

There is also substantial evidence that monoterpenes are effective in the prevention and treatment of cancer (Elson, C. E. and Yu, S. G., *J. Nutr.* 124: 607–614, 1994.). Thus, for example, limonene, perrilyl alcohol and geraniol have each been shown to have chemotherapeutic activity against a very broad range of mammalian cancers (see, for example, (1) limonene, Elegbede et al., *Carcinogenesis* 5:661–665, 1984; Elson et al., *Carcinogenesis* 9:331–332, 1988; Maltzman et al., *Carcinogenesis* 10:781–785, 1989; Wattenberg, L. W. and Coccia, J. B., *Carcinogenesis* 12:115–117, 1991; Wattenberg, L. W. and Coccia, J. B., *Carcinogenesis* 12:115–117, 1991; Haag et al., *Cancer Res.* 52:4021–4026, 1992; Crowell, P. L. and Gould, M. N., CRC *Crit. Rev. Oncogenesis* 5:1–22, 1994; (2) perillyl alcohol, Mills et al., *Cancer Res.* 55:979–983, 1995; Haag, J. D. and Gould, M. N., *Cancer Chemother. Pharmacol.* 34:477–483, 1994; Stark et al., *Cancer Lett.* 96:15–21, 1995 and (3) geraniol, Shoff et al., *Cancer Res.* 51:37–42, 1991; Yu et al., *J. Nutr.* 125:2763–2767, 1995; Burke et al., *Lipids* 32:151–156, 1997. ).

Cancer cells can be modified to produce therapeutic amounts of a monoterpene having anti-cancer properties by targeting the cognate monoterpene synthase protein to cancer cells, or by introducing a monoterpene synthase gene into cancer cells. This approach to cancer therapy is complicated, however, by the fact that the natural distribution of geranyl diphosphate synthase is largely restricted to plant species that produce abundant quantities of monoterpenes. Thus, animal cells do not naturally produce the monoterpene precursor geranyl diphosphate. Consequently, the genetic manipulation of cancer cells to produce endogenous monoterpenes having anti-cancer properties requires the introduction of a gene encoding geranyl diphosphate synthase, together with a gene encoding a monoterpene synthase that produces a monoterpene having anti-cancer properties. Similarly, if the protein targeting approach is utilized, both geranyl diphosphate synthase protein and monoterpene synthase protein must be targeted to cancer cells.

Standard protein targeting techniques can be used to introduce geranyl diphosphate synthase along with a monoterpene synthase, such as limonene synthase (Colby et al., *J. Biol. Chem.* 268:23016–23024, 1993), into animal cells with specific targeting to tumors. See, e.g., Wearley, L. L., *Critical Reviews in Therapeutic Drug Carrier Systems,* 8(4): 331–394, 1991; Sheldon, K et al., *Proc. Nat'l. Acad. Sci. USA.,* 92(6): 2056–2060, 1995. In addition, standard gene therapy techniques can be used to target a GPP synthase gene and a monoterpene synthase gene to cancerous cells for endogenous synthesis of monoterpenes having anti-cancer properties. For reviews of gene targeting technology see; Mahato R. I. et al., *Pharmaceutical Research* 14(7): 853–859, 1997; Rosenthal, F. M. and Mertelsmann, R., *Onkologie* 20(1): 26–34, 1997; Buckel, P., *Trends in Pharmacological Sciences* 17(12): 450–456, 1996; Roth, J. A. and Cristiano, R. J., *J. Nat'l Cancer Inst.* 89(1): 21–39, 1997; Ledley, F. D, *Pharmaceutical Research* 13(11): 1595–1614, 1996.

To date, extracts containing geranyl diphosphate synthase activity have been isolated from several plant sources, including grape (Clastre et al., *Plant Physiol.* 102:205–211, 1993); geranium (Suga, T. and Endo, T., *Phytochemistry* 30:1757–1761, 1991); sage (Croteau, R. and Purkett, P. T., *Arch. Biochem. Biophys.* 271:524–535, 1989) and *Lithospermum* (Heide, L. and Berger, U., *Arch. Biochem. Biophys.* 273:331–338, 1989). Only the enzyme from grape has been purified to homogeneity (Clastre et al., supra).

Table 1 summarizes the limited, available physical and chemical characteristics of geranyl diphosphate synthase isolated from several species.

TABLE 1

Deduced characteristics of geranyl diphosphate synthase[a]

| | |
|---|---|
| Native molecular weight | 66 kDa (V), 70 kDa (M), 73 kDa (L), 100 kDa (S) |
| Subunit configuration | monomer (V), dimer (M) |
| Cofactor requirements | Divalent metal ions required for catalysis $Mg^{2+}$ (M,S,L) or $Mn^{2+}$ (P,V) |
| Apparent $V_{max}$ | 9.4 μmol/min/mg (L) 150 nmol/h/mg (S) |
| Apparent $K_m$ | IPP 14 $_{\mu M}$ (L), 8.5$_{\mu M}$ (V), 7.3 $_{\mu M}$ (S) DMAPP 83$_{\mu M}$ (L), 56.8μM (V), 5.6$_{\mu M}$ (S) |
| pH optimum | 7.0 (S), 6.75 (L) |
| Isoelectric point | 4.95 (L) 5.42 (M18) |
| Inhibitors | Thiol-directed reagents (S), aminophenylethyl diphosphate (V), geranyl diphosphate (L, M) |

TABLE 1-continued

Deduced characteristics of geranyl diphosphate synthase[a]

| | |
|---|---|
| Catalytic enhancers under in vitro conditions | 1% v/v Triton-X 100 (P,V,M) |

[a]Geranyl diphosphate synthase characteristics are compiled from the data disclosed in: Croteau, R and Purkett, P. T., Arch. Biochem. Biophys. 271: 524–535, 1989; Heide, L. and Berger, U., Arch. Biochem. Biophys. 273: 331–338, 1989; Suga, T. and Endo, T., Phytochemistry 30: 1757–1761, 1991; Clastre et al., Plant Physiol. 102: 205–211, 1993. Uppercase letters in parentheses designate the following species: (M) *Mentha spicata*, (v) *Vitis vinifera*, (L) *Lithospermum erythrorhizon*, (S) *Salvia officinalis*, (P) *Pelargonium roseum*. (M18) refers to the "pseudomature" form of the GPP synthase encoded by cDNA clone Mp13.18 from *Mentha piperita* as described at page 8, supra.

These data reveal that the physical and chemical properties of geranyl diphosphate synthase vary considerably between species. For example, molecular mass varies from 66 kDa (in grape) to 100 kDa (in sage). Similarly, the isoelectric point of geranyl diphosphate synthase isolated from Lithospermum is 4.95, while the "pseudomature" form of mint geranyl diphosphate synthase (i.e., the protein encoded by the cDNA insert of clone Mp 13.18 having the first 48 amino acids deleted from the amino terminus) has an isoelectric point of 5.42. This variation in the physical and chemical properties of geranyl diphosphate synthase isolated from different species is reflected in the fact that the published purification protocols are each significantly different from the others.

Amino acid sequence data for geranyl diphosphate synthase has not been reported in the art. Although several DNA sequences encoding plant-derived FPP synthases and GGPP synthases are available (Scolnik, P. A. and Bartley, G. E., *Plant Mol. Biol. Report* 14:305–319, 1996), no genes for geranyl diphosphate synthase have thus far been reported.

SUMMARY OF THE INVENTION

In accordance with the foregoing, a cDNA encoding geranyl diphosphate synthase from peppermint has been isolated and sequenced, and the corresponding amino acid sequence has been deduced. Accordingly, the present invention relates to isolated DNA sequences which code for the expression of geranyl diphosphate synthase, such as the sequence designated SEQ ID No:1 which encodes geranyl diphosphate synthase from peppermint (*Mentha piperita*) (SEQ ID No:2). In other aspects, the present invention is directed to replicable recombinant cloning vehicles comprising a nucleic acid sequence, e.g., a DNA sequence which codes for a geranyl diphosphate synthase or for a base sequence sufficiently complementary to at least a portion of the geranyl diphosphate synthase DNA or RNA to enable hybridization therewith (e.g., antisense geranyl diphosphate synthase RNA or fragments of complementary geranyl diphosphate synthase DNA which are useful as polymerase chain reaction primers or as probes for geranyl diphosphate synthase or related genes). In yet other aspects of the invention, modified host cells are provided that have been transformed, transfected, infected and/or injected with a recombinant cloning vehicle and/or DNA sequence of the invention. Thus, the present invention provides for the recombinant expression of geranyl diphosphate synthases. The inventive concepts described herein may be used to facilitate the production, isolation and purification of significant quantities of recombinant geranyl diphosphate synthase (or of the primary enzyme product, geranyl diphosphate) for subsequent use, to obtain expression or enhanced expression of geranyl diphosphate synthase in plants, microorganisms or animals, or may be otherwise employed in an environment where the regulation or expression of geranyl diphosphate synthase is desired for the production of geranyl diphosphate synthase or the enzyme product, geranyl diphosphate, or its derivatives.

BRIEF DESCRIPTION OF THE DRAWINGS

The foregoing aspects and many of the attendant advantages of this invention will be better understood by reference to the following detailed description, when taken in conjunction with the accompanying drawings, wherein.

DETAILED DESCRIPTION OF THE PREFERRED EMBODIMENT

Figure 1:
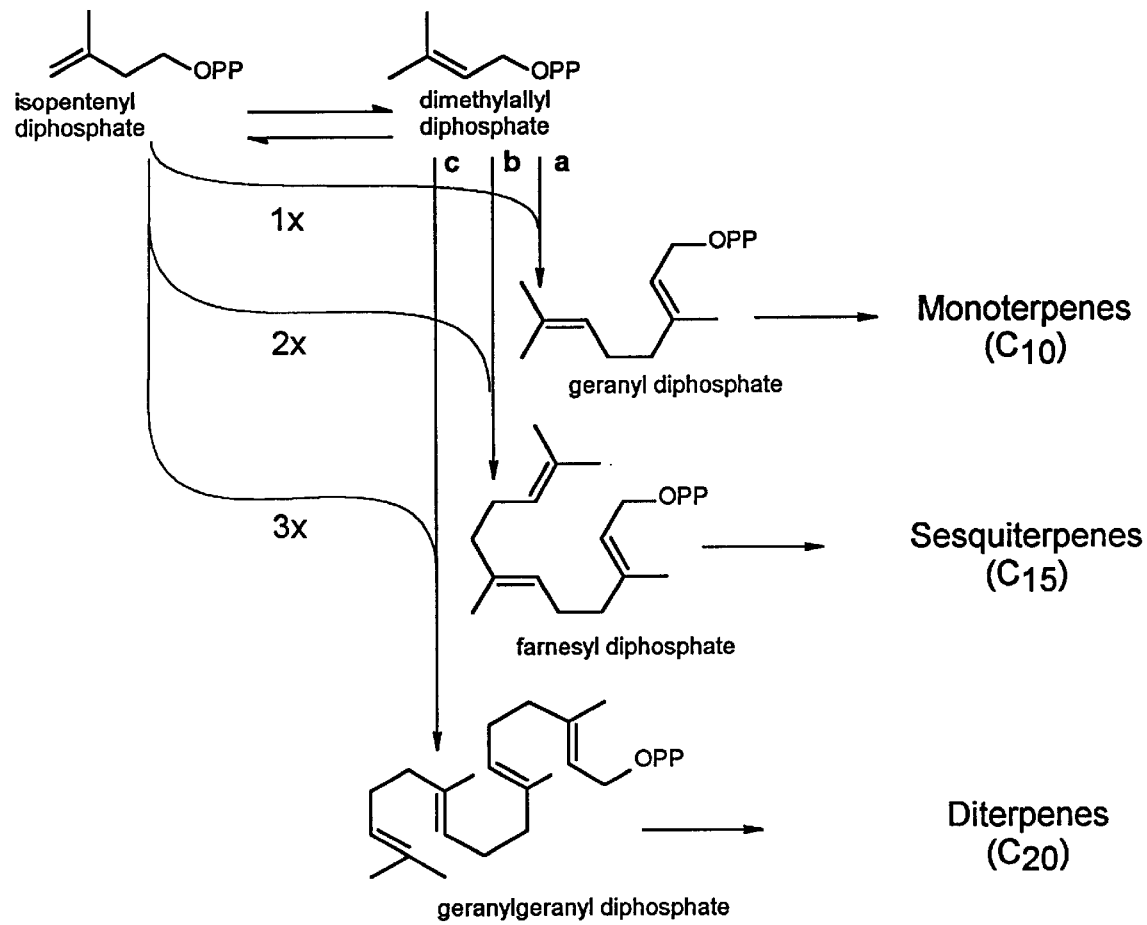
FIG. 1 shows the condensation reactions catalyzed by (a) geranyl diphosphate synthase, (b) farnesyl diphosphate synthase and (c) geranylgeranyl diphosphate synthase.
Figure 2:
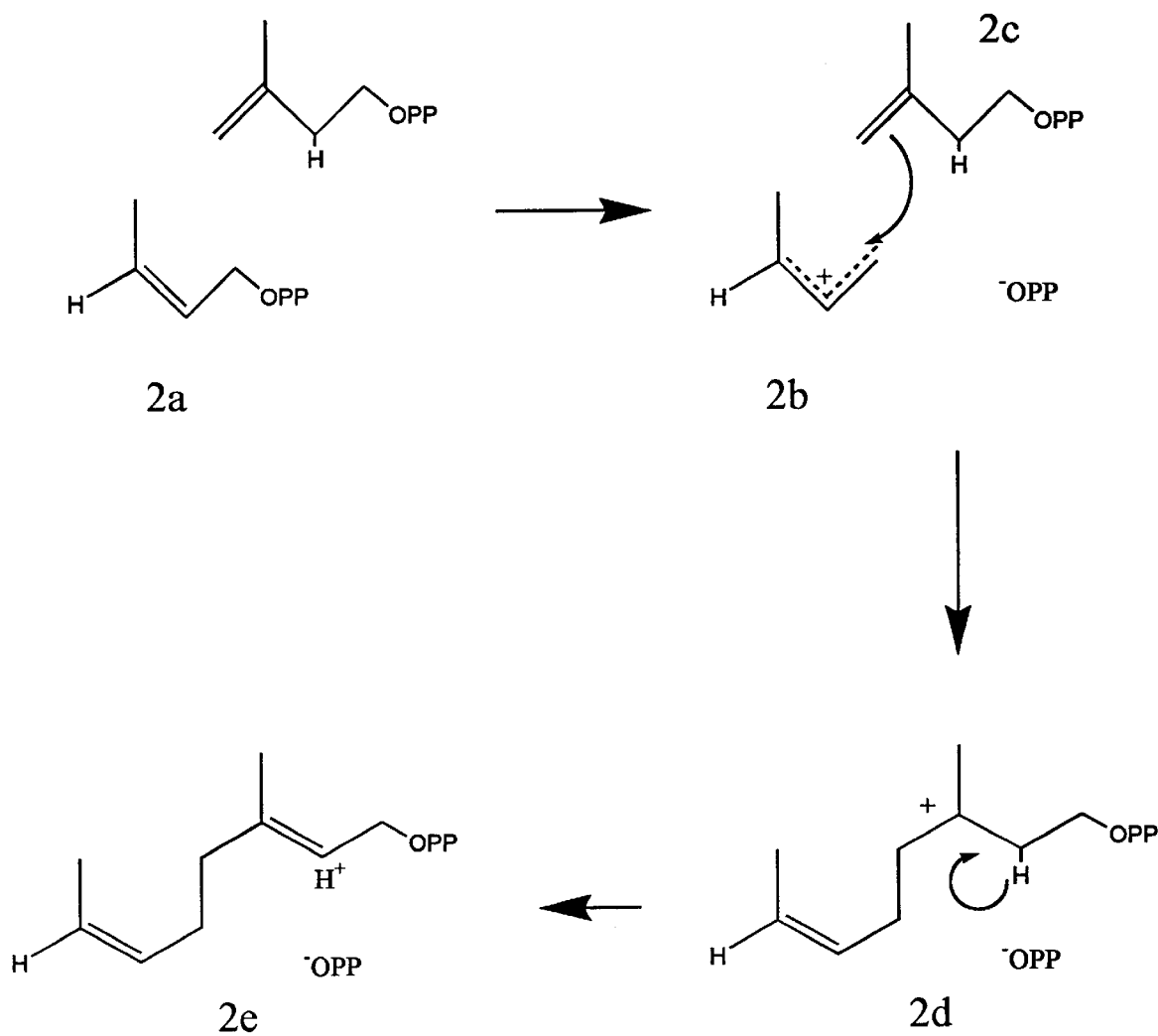
FIGS. 2a–2d show the reaction mechanism common to all prenyltransferases. The reaction catalyzed by geranyl diphosphate synthase is presented as illustrative of the general mechanism.

As used herein, the terms "amino acid" and "amino acids" refer to all naturally occurring L-α-amino acids or their residues. The amino acids are identified by either the single-letter or three-letter designations:

| Asp | D | aspartic acid  | Ile | I | isoleucine    |
|-----|---|----------------|-----|---|---------------|
| Thr | T | threonine      | Leu | L | leucine       |
| Ser | S | serine         | Tyr | Y | tyrosine      |
| Glu | E | glutamic acid  | Phe | F | phenylalanine |
| Pro | P | proline        | His | H | histidine     |
| Gly | G | glycine        | Lys | K | lysine        |
| Ala | A | alanine        | Arg | R | arginine      |
| Cys | C | cysteine       | Trp | W | tryptophan    |
| val | V | valine         | Gln | Q | glutamine     |
| Met | M | methionine     | Asn | N | asparagine    |

As used herein, the term "nucleotide" means a monomeric unit of DNA or RNA containing a sugar moiety (pentose), a phosphate and a nitrogenous heterocyclic base. The base is linked to the sugar moiety via the glycosidic carbon (1' carbon of pentose) and that combination of base and sugar is called a nucleoside. The base characterizes the nucleotide with the four bases of DNA being adenine ("A"), guanine ("G"), cytosine ("C") and thymine ("T"). Inosine ("I") is a synthetic base that can be used to substitute for any of the four, naturally-occurring bases (A, C, G or T). The four RNA bases are A,G,C and uracil ("U"). The nucleotide sequences described herein comprise a linear array of nucleotides connected by phosphodiester bonds between the 3' and 5' carbons of adjacent pentoses.

The term "percent identity" (% I) means the percentage of amino acids or nucleotides that occupy the same relative position when two amino acid sequences, or two nucleic acid sequences, are aligned side by side.

The term "percent similarity" (% S) is a statistical measure of the degree of relatedness of two compared protein sequences. The percent similarity is calculated by a computer program that assigns a numerical value to each compared pair of amino acids based on chemical similarity (e.g., whether the compared amino acids are acidic, basic, hydrophobic, aromatic, etc.) and/or evolutionary distance as measured by the minimum number of base pair changes that would be required to convert a codon encoding one member of a pair of compared amino acids to a codon encoding the other member of the pair. Calculations are made after a best fit alignment of the two sequences has been made empirically by iterative comparison of all possible alignments. (Henikoff, S. and Henikoff, J. G., Proc. Nat'l Acad Sci USA 89: 10915–10919, 1992).

As set forth herein, the percent identity and percent similarity values, at the amino acid level, between the Mentha GPP synthase disclosed herein (SEQ ID No:2) and GGPP synthases are averages of the values obtained from individual, pairwise comparisons made between the deduced amino acid sequence of the Mentha GPP synthase disclosed herein (SEQ ID No:2) and the GGPP synthases set forth in Table 2. Similarly, as set forth herein, the percent identity and percent similarity values, at the amino acid level, between the Mentha GPP synthase disclosed herein (SEQ ID No:2) and FPP synthases are averages of the values obtained from individual, pairwise comparisons made between the deduced amino acid sequence of the Mentha GPP synthase disclosed herein (SEQ ID No:2) and the FPP synthases set forth in Table 2. The % I and % S values set forth in Table 2 are the values obtained from the individual, pairwise comparisons of the Mentha GPP synthase protein sequence (SEQ ID No: 2) and each of the sequences listed in Table 2.

TABLE 2

| Monoterpene Synthase | Species | Accession Number | % S | % I |
|---|---|---|---|---|
| GGPP Synthase | Capsicum annum | X80267 | 54 | 30 |
| GGPP synthasse | Catharanthus roseus | X92893 | 56 | 29 |
| GGPP synthase | Arabidopsis thaliana | L25813 | 53 | 26 |
| FPP synthase | Zea mays | L39789 | 41 | 17 |
| FPP synthase | Lupinus albus | U15777 | 38 | 15 |

% S means the percent similarity with the deduced amino acid sequence of the Mentha GPP synthase disclosed herein (SEQ ID No:2).
% I means the percent identity with the deduced amino acid sequence of the Mentha GPP synthase disclosed herein (SEQ ID No:2).
Accession numbers refer to the accession numbers for the GemBank sequence database.

"Oligonucleotide" refers to short length single or double stranded sequences of deoxyribonucleotides linked via phosphodiester bonds. The oligonucleotides are chemically synthesized by known methods and purified, for example, on polyacrylamide gels.

The term "geranyl diphosphate synthase" is used herein to mean an enzyme capable of catalyzing the condensation of dimethylallyl diphosphate (DMAPP) and isopentenyl diphosphate (IPP) to form geranyl diphosphate, the immediate acyclic precursor of the monoterpenes, as described herein.

The terms "alteration", "amino acid sequence alteration", "variant" and "amino acid sequence variant" refer to geranyl diphosphate synthase molecules with some differences in their amino acid sequences as compared to native geranyl diphosphate synthase. Ordinarily, the variants will possess at least about 70% homology with native geranyl diphosphate synthase, and preferably they will be at least about 80% homologous with native geranyl diphosphate synthase. The amino acid sequence variants of geranyl diphosphate synthase falling within this invention possess substitutions, deletions, and/or insertions at certain positions. Sequence variants of geranyl diphosphate synthase may be used to attain desired enhanced or reduced enzymatic activity, modified regiochemistry or stereochemistry, or altered substrate utilization or product distribution.

Substitutional geranyl diphosphate synthase variants are those that have at least one amino acid residue in the native geranyl diphosphate synthase sequence removed and a different amino acid inserted in its place at the same position. The substitutions may be single, where only one amino acid in the molecule has been substituted, or they may be multiple, where two or more amino acids have been substituted in the same molecule. Substantial changes in the activity of the geranyl diphosphate synthase molecule may be obtained by substituting an amino acid with a side chain that is significantly different in charge and/or structure from that of the native amino acid. This type of substitution would be expected to affect the structure of the polypeptide backbone and/or the charge or hydrophobicity of the molecule in the area of the substitution.

Moderate changes in the activity of the geranyl diphosphate synthase molecule would be expected by substituting an amino acid with a side chain that is similar in charge and/or structure to that of the native molecule. This type of substitution, referred to as a conservative substitution, would not be expected to substantially alter either the structure of the polypeptide backbone or the charge or hydrophobicity of the molecule in the area of the substitution.

Insertional geranyl diphosphate synthase variants are those with one or more amino acids inserted immediately adjacent to an amino acid at a particular position in the native geranyl diphosphate synthase molecule. Immediately adjacent to an amino acid means connected to either the α-carboxy or α-amino functional group of the amino acid. The insertion may be one or more amino acids. Ordinarily, the insertion will consist of one or two conservative amino acids. Amino acids similar in charge and/or structure to the amino acids adjacent to the site of insertion are defined as conservative. Alternatively, this invention includes insertion of an amino acid with a charge and/or structure that is substantially different from the amino acids adjacent to the site of insertion.

Deletional variants are those where one or more amino acids in the native geranyl diphosphate synthase molecule have been removed. Ordinarily, deletional variants will have one or two amino acids deleted in a particular region of the geranyl diphosphate synthase molecule.

The terms "biological activity", "biologically active", "activity" and "active" refer to the ability of the geranyl diphosphate synthase molecule to condense dimethylallyl diphosphate (DMAPP) and isopentenyl diphosphate (IPP) to form geranyl diphosphate, as measured in an enzyme activity assay, such as the assay described in Example 1 below. Amino acid sequence variants of geranyl diphosphate synthase may have desirable altered biological activity including, for example, altered reaction kinetics, substrate utilization product distribution or other characteristics such as regiochemistry and stereochemistry.

The terms "DNA sequence encoding", "DNA encoding" and "nucleic acid encoding" refer to the order or sequence of deoxyribonucleotides along a strand of deoxyribonucleic acid. The order of these deoxyribonucleotides determines the order of amino acids along the translated polypeptide chain. The DNA sequence thus codes for the amino acid sequence.

The terms "replicable expression vector" and "expression vector" refer to a piece of DNA, usually double-stranded, which may have inserted into it a piece of foreign DNA. Foreign DNA is defined as heterologous DNA, which is DNA not naturally found in the host. The vector is used to transport the foreign or heterologous DNA into a suitable host cell. Once in the host cell, the vector can replicate independently of or coincidental with the host chromosomal DNA, and several copies of the vector and its inserted (foreign) DNA may be generated. In addition, the vector contains the necessary elements that permit translating the foreign DNA into a polypeptide. Many molecules of the polypeptide encoded by the foreign DNA can thus be rapidly synthesized.

The terms "transformed host cell," "transformed" and "transformation" refer to the introduction of DNA into a cell. The cell is termed a "host cell", and it may be a prokaryotic or a eukaryotic cell. Typical prokaryotic host cells include various strains of E. coli. Typical eukaryotic host cells are plant cells, such as maize cells, yeast cells, insect cells or animal cells. The introduced DNA is usually in the form of a vector containing an inserted piece of DNA. The introduced DNA sequence may be from the same species as the host cell or from a different species from the host cell, or it may be a hybrid DNA sequence, containing some foreign DNA and some DNA derived from the host species.

In accordance with the present invention, a cDNA encoding geranyl diphosphate synthase was isolated and sequenced in the following manner. Geranyl diphosphate synthase is located exclusively in the glandular trichome secretory cells and catalyzes the formation of geranyl diphosphate in these essential oil species. These secretory cell clusters were isolated from *Mentha spicata* by known methods and geranyl diphosphate synthase was purified therefrom utilizing a novel purification protocol consisting of a dye-ligand chromatography step, and an anion exchange chromatography step followed by preparative SDS-PAGE. The limited amount of purified geranyl diphosphate synthase yielded the sequence of a nine amino acid peptide (SEQ. ID. No:3). This sequence information was insufficient to permit a reverse genetic approach to cloning the geranyl diphosphate synthase cDNA, i.e., there was insufficient amino acid sequence to permit the construction of degenerate oligonucleotide probes that were sufficiently specific to be effective as probes.

Consequently, total RNA was extracted from isolated trichome secretory cells derived from *Mentha piperita* and mRNA was purified therefrom. The secretory cell mRNA served as the substrate for the synthesis of a cDNA library by standard means. One hundred, randomly selected cDNA clones were sequenced and one clone showed low homology to plant-derived geranylgeranyl diphosphate synthases (~28% identity; ~54% similarity). Sequence information derived from this "prenyltransferase-like" cDNA was used to construct PCR primers (SEQ ID No:4 and SEQ ID No:5) which were, in turn, used to amplify a 113 bp fragment (SEQ ID No:6) of the "prenyltransferase-like" cDNA which was used as a probe to isolate twenty seven additional, homologous clones from the glandular trichome, secretory cell library. Sequencing revealed that the twenty seven clones represented three alleles. The biological activity of one clone from each of the three allele groups was tested by measuring geranyl diphosphate activity in supernatant derived from *E. coli* individually expressing each of the three, representative cDNAs. The clone showing the highest level of geranyl diphosphate synthase activity (designated Mp13.18) was completely sequenced (SEQ ID No: 1) and its identity as a geranyl diphosphate synthase clone was confirmed by comparing the deduced geranyl diphosphate synthase protein sequence with the sequence of the nine amino acid peptide (SEQ ID No:3) derived from geranyl diphosphate synthase protein purified from *Mentha spicata*.

Additionally, the sequence of an eight amino acid peptide (SEQ ID No:7), derived from geranyl diphosphate synthase protein purified from *Mentha spicata*, was obtained subsequent to the cloning of geranyl diphosphate synthase. The sequences of both the nine amino acid peptide (SEQ ID No:3), and the eight amino acid peptide (SEQ ID No:7) exactly matched the corresponding regions of the protein sequence deduced from the cloned geranyl diphosphate synthase cDNA (SEQ ID No:2, amino acids 254 thru 262, and 184 thru 191, respectively). The observation that the peptide sequences derived from purified *Mentha spicata* geranyl diphosphate synthase perfectly matched the corresponding regions of the cloned *Mentha piperita* geranyl diphosphate synthase is consistent with the genetic relationship between the two species: peppermint (*Mentha piperita*) is a hexaploid species produced by crossing *Mentha aquatica* with tetraploid *Mentha spicata* (Harley and Brighton, *Bot. J. Linn. Soc.* 74:71–96 [1977]). In effect, hexaploid peppermint contains the complete genome of tetraploid spearmint.

The isolation of the geranyl diphosphate synthase cDNA permits the development of an efficient expression system for this functional enzyme; provides a useful tool for examining the developmental regulation of monoterpene biosynthesis and permits the isolation of other geranyl diphosphate synthases. The isolation of the geranyl diphosphate synthase cDNA also permits the transformation of a wide range of organisms in order to introduce monoterpene biosynthesis de novo, or to modify endogenous monoterpene biosynthesis.

Although the geranyl diphosphate synthase protein set forth in SEQ ID No:2 directs the enzyme to plastids, substitution of the putative targeting sequence (SEQ ID No:2, amino acids 1 to 48) with other transport sequences well known in the art (see, e.g., von Heijne G et al., *Eur. J. Biochem* 180: 535–545, 1989; Stryer, *Biochemistry* W. H. Freeman and Company, New York, N.Y., p. 769 [1988]) may be employed to direct the geranyl diphosphate synthase to other cellular or extracellular locations.

In addition to the native geranyl diphosphate synthase amino acid sequence of SEQ ID No:2 encoded by the cDNA insert of plasmid Mp 13.18 (SEQ ID No:1), sequence variants produced by deletions, substitutions, mutations and/ or insertions are intended to be within the scope of the invention except insofar as limited by the prior art. Geranyl diphosphate synthase amino acid sequence variants may be constructed by mutating the DNA sequence that encodes wild-type geranyl diphosphate synthase, such as by using techniques commonly referred to as site-directed mutagenesis. Various polymerase chain reaction (PCR) methods now well known in the field, such as a two primer system like the Transformer Site-Directed Mutagenesis kit from Clontech, may be employed for this purpose.

Following denaturation of the target plasmid in this system, two primers are simultaneously annealed to the plasmid; one of these primers contains the desired site-directed mutation, the other contains a mutation at another point in the plasmid resulting in elimination of a restriction site. Second strand synthesis is then carried out, tightly linking these two mutations, and the resulting plasmids are transformed into a mutS strain of *E. coli*. Plasmid DNA is isolated from the transformed bacteria, restricted with the relevant restriction enzyme (thereby linearizing the unmutated plasmids), and then retransformed into *E. coli*. This system allows for generation of mutations directly in an expression plasmid, without the necessity of subcloning or generation of single-stranded phagemids. The tight linkage of the two mutations and the subsequent linearization of unmutated plasmids results in high mutation efficiency and allows minimal screening. Following synthesis of the initial restriction site primer, this method requires the use of only one new primer type per mutation site. Rather than prepare each positional mutant separately, a set of "designed degenerate" oligonucleotide primers can be synthesized in order to introduce all of the desired mutations at a given site simultaneously. Transformants can be screened by sequencing the plasmid DNA through the mutagenized region to identify and sort mutant clones. Each mutant DNA can then be restricted and analyzed by electrophoresis on Mutation Detection Enhancement gel (J. T. Baker) to confirm that no other alterations in the sequence have occurred (by band shift comparison to the unmutagenized control).

The verified mutant duplexes can be cloned into a replicable expression vector, if not already cloned into a vector of this type, and the resulting expression construct used to transform *E. coli*, such as strain *E. coli* BL21(DE3)pLysS, for high level production of the mutant protein, and subsequent purification thereof. The method of FAB-MS mapping can be employed to rapidly check the fidelity of mutant expression. This technique provides for sequencing segments throughout the whole protein and provides the necessary confidence in the sequence assignment. In a mapping experiment of this type, protein is digested with a protease (the choice will depend on the specific region to be modified since this segment is of prime interest and the remaining map should be identical to the map of unmutagenized protein). The set of cleavage fragments is fractionated by microbore HPLC (reversed phase or ion exchange, again depending on the specific region to be modified) to provide several peptides in each fraction, and the molecular weights of the peptides are determined by FAB-MS. The masses are then compared to the molecular weights of peptides expected from the digestion of the predicted sequence, and the correctness of the sequence quickly ascertained. Since this mutagenesis approach to protein modification is directed, sequencing of the altered peptide should not be necessary if the MS agrees with prediction. If necessary to verify a changed residue, CAD-tandem MS/MS can be employed to sequence the peptides of the mixture in question, or the target peptide purified for subtractive Edman degradation or carboxypeptidase Y digestion depending on the location of the modification.

In the design of a particular site directed mutant, it is generally desirable to first make a non-conservative substitution (e.g., Ala for Cys, His or Glu) and determine if activity is greatly impaired as a consequence. The properties of the mutagenized protein are then examined with particular attention to the kinetic parameters of $K_m$ and $k_{cat}$ as sensitive indicators of altered function, from which changes in binding and/or catalysis per se may be deduced by comparison to the native enzyme. If the residue is by this means demonstrated to be important by activity impairment, or knockout, then conservative substitutions can be made, such as Asp for Glu to alter side chain length, Ser for Cys, or Arg for His. For hydrophobic segments, it is largely size that will be altered, although aromatics can also be substituted for alkyl side chains. Changes in the normal product distribution can indicate which step(s) of the reaction sequence have been altered by the mutation.

Other site directed mutagenesis techniques may also be employed with the nucleotide sequences of the invention. For example, restriction endonuclease digestion of DNA followed by ligation may be used to generate geranyl diphosphate synthase deletion variants, as described in section 15.3 of Sambrook et al. (*Molecular Cloning: A Laboratory Manual*, 2nd Ed., Cold Spring Harbor Laboratory Press, New York, N.Y. [1989]). A similar strategy may be used to construct insertion variants, as described in section 15.3 of Sambrook et al., supra.

Oligonucleotide-directed mutagenesis may also be employed for preparing substitution variants of this invention. It may also be used to conveniently prepare the deletion and insertion variants of this invention. This technique is well known in the art as described by Adelman et al. (*DNA* 2:183 [1983]). Generally, oligonucleotides of at least 25 nucleotides in length are used to insert, delete or substitute two or more nucleotides in the geranyl diphosphate synthase molecule. An optimal oligonucleotide will have 12 to 15 perfectly matched nucleotides on either side of the nucleotides coding for the mutation. To mutagenize the wild-type geranyl diphosphate synthase, the oligonucleotide is annealed to the single-stranded DNA template molecule under suitable hybridization conditions. A DNA polymerizing enzyme, usually the Klenow fragment of *E. coli* DNA polymerase I, is then added. This enzyme uses the oligonucleotide as a primer to complete the synthesis of the mutation-bearing strand of DNA. Thus, a heteroduplex molecule is formed such that one strand of DNA encodes the wild-type geranyl diphosphate synthase inserted in the vector, and the second strand of DNA encodes the mutated form of geranyl diphosphate synthase inserted into the same vector. This heteroduplex molecule is then transformed into a suitable host cell.

Mutants with more than one amino acid substituted may be generated in one of several ways. If the amino acids are located close together in the polypeptide chain, they may be mutated simultaneously using one oligonucleotide that codes for all of the desired amino acid substitutions. If however, the amino acids are located some distance from each other (separated by more than ten amino acids, for example) it is more difficult to generate a single oligonucleotide that encodes all of the desired changes. Instead, one of two alternative methods may be employed. In the first method, a separate oligonucleotide is generated for each amino acid to be substituted. The oligonucleotides are then annealed to the single-stranded template DNA simultaneously, and the second strand of DNA that is synthesized from the template will encode all of the desired amino acid substitutions. An alternative method involves two or more rounds of mutagenesis to produce the desired mutant. The first round is as described for the single mutants: wild-type geranyl diphosphate synthase DNA is used for the template, an oligonucleotide encoding the first desired amino acid substitution(s) is annealed to this template, and the heteroduplex DNA molecule is then generated. The second round of mutagenesis utilizes the mutated DNA produced in the first round of mutagenesis as the template. Thus, this template already contains one or more mutations. The oligonucleotide encoding the additional desired amino acid substitution(s) is then annealed to this template, and the resulting strand of DNA now encodes mutations from both the first and second rounds of mutagenesis. This resultant DNA can be used as a template in a third round of mutagenesis, and so on.

The gene encoding geranyl diphosphate synthase may be incorporated into any organism (intact plant, animal, microbe), or cell culture derived therefrom, that produces dimethylallyl diphosphate and isopentenyl diphosphate to effect the conversion of these primary substrates to geranyl diphosphate and its subsequent metabolic products, depending on the organism. The geranyl diphosphate synthase gene may be introduced into any organism for a variety of purposes including, but not limited to: production or modification of flavor and aroma properties; improvement of defense capability; the alteration of other ecological interactions mediated by geranyl diphosphate and its derivatives; selective destruction or inhibition of the growth, development or division of cancerous cells; or the production of geranyl diphosphate and its derivatives.

Eukaryotic expression systems may be utilized for geranyl diphosphate synthase production since they are capable of carrying out any required posttranslational modifications and of directing the enzyme to the proper membrane location. A representative eukaryotic expression system for this purpose uses the recombinant baculovirus, *Autographa californica* nuclear polyhedrosis virus (AcNPV; M. D. Summers and G. E. Smith, *A Manual of Methods for Baculovirus Vectors and Insect Cell Culture Procedures* [1986]; Luckow et al., *Bio-technology* 6:47–55 [1987]) for expression of the geranyl diphosphate synthase of the invention. Infection of insect cells (such as cells of the species *Spodoptera frugiperda*) with the recombinant baculoviruses allows for the production of large amounts of the geranyl diphosphate synthase protein. In addition, the baculovirus system has other important advantages for the production of recombinant geranyl diphosphate synthase. For example, baculoviruses do not infect humans and can therefore be safely handled in large quantities. In the baculovirus system, a DNA construct is prepared including a DNA segment encoding geranyl diphosphate synthase and a vector. The vector may comprise the polyhedron gene promoter region of a baculovirus, the baculovirus flanking sequences necessary for proper cross-over during recombination (the flanking sequences comprise about 200–300 base pairs adjacent to the promoter sequence) and a bacterial origin of replication which permits the construct to replicate in bacteria. The vector is constructed so that (i) the DNA segment is placed adjacent (or operably linked or "downstream" or "under the control of") to the polyhedron gene promoter and (ii) the promoter/geranyl diphosphate synthase combination is flanked on both sides by 200–300 base pairs of baculovirus DNA (the flanking sequences).

To produce the geranyl diphosphate synthase DNA construct, a cDNA clone encoding the full length geranyl diphosphate synthase is obtained using methods such as those described herein. The DNA construct is contacted in a host cell with baculovirus DNA of an appropriate baculovirus (that is, of the same species of baculovirus as the promoter encoded in the construct) under conditions such that recombination is effected. The resulting recombinant baculoviruses encode the full geranyl diphosphate synthase. For example, an insect host cell can be cotransfected or transfected separately with the DNA construct and a functional baculovirus. Resulting recombinant baculoviruses can then be isolated and used to infect cells to effect production of the geranyl diphosphate synthase. Host insect cells include, for example, *Spodoptera frugiperda* cells, that are capable of producing a baculovirus-expressed geranyl diphosphate synthase. Insect host cells infected with a recombinant baculovirus of the present invention are then cultured under conditions allowing expression of the baculovirus-encoded geranyl diphosphate synthase. Geranyl diphosphate synthase thus produced is then extracted from the cells using methods known in the art.

Other eukaryotic microbes such as yeasts may also be used to practice this invention. The baker's yeast *Saccharomyces cerevisiae*, is a commonly used yeast, although several other strains are available. The plasmid YRp7 (Stinchcomb et al., *Nature* 282:39 [1979]; Kingsman et al., Gene 7:141 [1979]; Tschemper et al., Gene 10:157 [1980]) is commonly used as an expression vector in Saccharomyces. This plasmid contains the trp1 gene that provides a selection marker for a mutant strain of yeast lacking the ability to grow in tryptophan, such as strains ATCC No. 44,076 and PEP4-1 (Jones, *Genetics* 85:12 [1977]). The presence of the trp1 lesion as a characteristic of the yeast host cell genome then provides an effective environment for detecting transformation by growth in the absence of tryptophan. Yeast host cells are generally transformed using the polyethylene glycol method, as described by Hinnen (*Proc. Natl. Acad. Sci. USA* 75:1929 [1978]. Additional yeast transformation protocols are set forth in Gietz et al., N. A. R 20(17):1425, 1992; Reeves et al., *FEMS* 99:193–197, 1992.

Suitable promoting sequences in yeast vectors include the promoters for 3-phosphoglycerate kinase (Hitzeman et al.,*J. Biol. Chem.* 255:2073 [1980]) or other glycolytic enzymes (Hess et al., *J. Adv. Enzyme Reg.* 7:149 [1968]; Holland et al., *Biochemistry* 17:4900 [1978]), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In the construction of suitable expression plasmids, the termination sequences associated with these genes are also ligated into the expression vector 3' of the sequence desired to be expressed to provide polyadenylation of the mRNA and termination. Other promoters that have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing yeast-compatible promoter, origin of replication and termination sequences is suitable.

Cell cultures derived from multicellular organisms, such as plants, may be used as hosts to practice this invention. Transgenic plants can be obtained, for example, by transferring plasmids that encode geranyl diphosphate synthase and a selectable marker gene, e.g., the kan gene encoding resistance to kanamycin, into *Agrobacterium tumifaciens* containing a helper Ti plasmid as described in Hoeckema et al., *Nature* 303:179–181 [1983] and culturing the Agrobacterium cells with leaf slices of the plant to be transformed as described by An et al.,*Plant Physiology* 81:301–305 [1986]. Transformation of cultured plant host cells is normally accomplished through *Agrobacterium tumifaciens*, as described above. Cultures of mammalian host cells and other host cells that do not have rigid cell membrane barriers are usually transformed using the calcium phosphate method as originally described by Graham and Van der Eb (*Virology* 52:546 [1978]) and modified as described in sections 16.32–16.37 of Sambrook et al., supra. However, other methods for introducing DNA into cells such as Polybrene (Kawai and Nishizawa, *Mol. Cell. Biol.* 4:1172 [1984]), protoplast fusion (Schaffner, *Proc. Natl. Acad. Sci. USA* 77:2163 [1980]), electroporation (Neumann et al., *EMBO J.* 1:841 [1982]), and direct microinjection into nuclei (Capecchi, *Cell* 22:479 [1980]) may also be used. Additionally, animal transformation strategies are reviewed in Monastersky G. M. and Robl, J. M., *Strategies in Transgenic Animal Science*, ASM Press, Washington, D.C., 1995. Transformed plant calli may be selected through the selectable marker by growing the cells on a medium containing, e.g., kanamycin, and appropriate amounts of phytohormone such as naphthalene acetic acid and benzyladenine for callus and shoot induction. The plant cells may then be regenerated and the resulting plants transferred to soil using techniques well known to those skilled in the art.

In addition, a gene regulating geranyl diphosphate synthase production can be incorporated into the plant along with a necessary promoter which is inducible. In the practice of this embodiment of the invention, a promoter that only responds to a specific external or internal stimulus is fused to the target cDNA. Thus, the gene will not be transcribed except in response to the specific stimulus. As long as the gene is not being transcribed, its gene product is not produced.

An illustrative example of a responsive promoter system that can be used in the practice of this invention is the glutathione-S-transferase (GST) system in maize. GSTs are a family of enzymes that can detoxify a number of hydrophobic electrophilic compounds that often are used as pre-emergent herbicides (Weigand et al., *Plant Molecular Biology* 7:235–243 [1986]). Studies have shown that the GSTs are directly involved in causing this enhanced herbicide tolerance. This action is primarily mediated through a specific 1.1 kb mRNA transcription product. In short, maize has a naturally occurring quiescent gene already present that can respond to external stimuli and that can be induced to produce a gene product. This gene has previously been identified and cloned. Thus, in one embodiment of this invention, the promoter is removed from the GST responsive gene and attached to a geranyl diphosphate synthase gene that previously has had its native promoter removed. This engineered gene is the combination of a promoter that responds to an external chemical stimulus and a gene responsible for successful production of geranyl diphosphate synthase.

In addition to the methods described above, several methods are known in the art for transferring cloned DNA into a wide variety of plant species, including gymnosperms, angiosperms, monocots and dicots (see, e.g., Glick and Thompson, eds.,*Methods in Plant Molecular Biology*, CRC Press, Boca Raton, Fla. [1993]). Representative examples include electroporation-facilitated DNA uptake by protoplasts (Rhodes et al., *Science* 240(4849):204–207 [1988]); treatment of protoplasts with polyethylene glycol (Lyznik et al., *Plant Molecular Biology* 13:151–161 [1989]); and bombardment of cells with DNA laden microprojectiles (Klein et al., *Plant Physiol.* 91:440–444 [1989] and Boynton et al., *Science* 240(4858):1534–1538 [1988]). Additionally, plant transformation strategies and techniques are reviewed in Birch, R. G., *Ann Rev Plant Phys Plant Mol Biol* 48:297 (1997); Forester et al., *Exp. Agric.* 33:15–33 (1997). Minor variations make these technologies applicable to a broad range of plant species.

Each of these techniques has advantages and disadvantages. In each of the techniques, DNA from a plasmid is genetically engineered such that it contains not only the gene of interest, but also selectable and screenable marker genes. A selectable marker gene is used to select only those cells that have integrated copies of the plasmid (the construction is such that the gene of interest and the selectable and screenable genes are transferred as a unit). The screenable gene provides another check for the successful culturing of only those cells carrying the genes of interest. A commonly used selectable marker gene is neomycin phosphotransferase II (NPT II). This gene conveys resistance to kanamycin, a compound that can be added directly to the growth media on which the cells grow. Plant cells are normally susceptible to kanamycin and, as a result, die. The presence of the NPT II gene overcomes the effects of the kanamycin and each cell with this gene remains viable.

Another selectable marker gene which can be employed in the practice of this invention is the gene which confers resistance to the herbicide glufosinate (Basta). A screenable gene commonly used is the β-glucuronidase gene (GUS). The presence of this gene is characterized using a histochemical reaction in which a sample of putatively transformed cells is treated with a GUS assay solution. After an appropriate incubation, the cells containing the GUS gene turn blue. Preferably, the plasmid will contain both selectable and screenable marker genes.

The plasmid containing one or more of these genes is introduced into either plant protoplasts or callus cells by any of the previously mentioned techniques. If the marker gene is a selectable gene, only those cells that have incorporated the DNA package survive under selection with the appropriate phytotoxic agent. Once the appropriate cells are identified and propagated, plants are regenerated. Progeny from the transformed plants must be tested to insure that the DNA package has been successfully integrated into the plant genome.

Mammalian host cells may also be used in the practice of the invention. Examples of suitable mammalian cell lines include monkey kidney CVI line transformed by SV40 (COS-7, ATCC CRL 1651); human embryonic kidney line 293S (Graham et al., *J. Gen. Virol.* 36:59 [1977]); baby hamster kidney cells (BHK, ATCC CCL 10); Chinese hamster ovary cells (Urlab and Chasin, *Proc. Natl. Acad. Sci USA* 77:4216 [1980]); mouse sertoli cells (TM4, Mather, *Biol. Reprod.* 23:243 [1980]); monkey kidney cells (CVI-76, ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor cells (MMT 060562, ATCC CCL 51); rat hepatoma cells (HTC, MI.54, Baumann et al., *J. Cell Biol.* 85:1 [1980]); and TRI cells (Mather et al., *Annals N.Y. Acad. Sci.* 383:44 [1982]). Expression vectors for these cells ordinarily include (if necessary) DNA sequences for an origin of replication, a promoter located in front of the gene to be expressed, a ribosome binding site, an RNA splice site, a polyadenylation site, and a transcription terminator site.

Promoters used in mammalian expression vectors are often of viral origin. These viral promoters are commonly derived from polyoma virus, Adenovirus 2, and most frequently Simian Virus 40 (SV40). The SV40 virus contains two promoters that are termed the early and late promoters. These promoters are particularly useful because they are both easily obtained from the virus as one DNA fragment that also contains the viral origin of replication (Fiers et al., *Nature* 273:113 [1978]). Smaller or larger SV40 DNA fragments may also be used, provided they contain the approximately 250-bp sequence extending from the HindIII site toward the BglI site located in the viral origin of replication.

Alternatively, promoters that are naturally associated with the foreign gene (homologous promoters) may be used provided that they are compatible with the host cell line selected for transformation.

An origin of replication may be obtained from an exogenous source, such as SV40 or other virus (e.g., Polyoma, Adeno, VSV, BPV) and inserted into the cloning vector. Alternatively, the origin of replication may be provided by the host cell chromosomal replication mechanism. If the vector containing the foreign gene is integrated into the host cell chromosome, the latter is often sufficient.

The use of a secondary DNA coding sequence can enhance production levels of geranyl diphosphate synthase in transformed cell lines. The secondary coding sequence typically comprises the enzyme dihydrofolate reductase (DHFR). The wild-type form of DHFR is normally inhibited by the chemical methotrexate (MTX). The level of DHFR expression in a cell will vary depending on the amount of MTX added to the cultured host cells. An additional feature of DHFR that makes it particularly useful as a secondary sequence is that it can be used as a selection marker to identify transformed cells. Two forms of DHFR are available for use as secondary sequences, wild-type DHFR and MTX-resistant DHFR. The type of DHFR used in a particular host cell depends on whether the host cell is DHFR deficient (such that it either produces very low levels of DHFR endogenously, or it does not produce functional DHFR at all). DHFR-deficient cell lines such as the CHO cell line described by Urlaub and Chasin, supra, are transformed with wild-type DHFR coding sequences. After transformation, these DHFR-deficient cell lines express functional DHFR and are capable of growing in a culture medium lacking the nutrients hypoxanthine, glycine and thymidine. Nontransformed cells will not survive in this medium.

The MTX-resistant form of DHFR can be used as a means of selecting for transformed host cells in those host cells that endogenously produce normal amounts of functional DHFR that is MTX sensitive. The CHO-K1 cell line (ATCC No. CL 61) possesses these characteristics, and is thus a useful cell line for this purpose. The addition of MTX to the cell culture medium will permit only those cells transformed with the DNA encoding the MTX-resistant DHFR to grow. The nontransformed cells will be unable to survive in this medium.

Prokaryotes may also be used as host cells for the initial cloning steps of this invention. They are particularly useful for rapid production of large amounts of DNA, for production of single-stranded DNA templates used for site-directed mutagenesis, for screening many mutants simultaneously, and for DNA sequencing of the mutants generated. Suitable prokaryotic host cells include *E. coli* K12 strain 294 (ATCC No. 31,446), *E. coli* strain W3110 (ATCC No. 27,325) *E. coil* X1776 (ATCC No. 31,537), and *E. coil* B; however many other strains of *E. coli*, such as HB101, JM101, NM522, NM538, NM539, and many other species and genera of prokaryotes including bacilli such as *Bacillus subtilis*, other enterobacteriaceae such as *Salmonella typhimurium* or *Serratia marcesans*, and various Pseudomonas species may all be used as hosts. Prokaryotic host cells or other host cells with rigid cell walls are preferably transformed using the calcium chloride method as described in section 1.82 of Sambrook et al., supra. Alternatively, electroporation may be used for transformation of these cells. Prokaryote transformation techniques are set forth in Dower, W. J., in Genetic Engineering, Principles and Methods, 12:275–296, Plenum Publishing Corp., 1990; Hanahan et al., *Meth. Enxymol.*, 204:63, 1991.

As a representative example, cDNA sequences encoding geranyl diphosphate synthase may be transferred to the (His)$_6$. Tag pET vector commercially available (from Novagen) for overexpression in *E. coli* as heterologous host. This pET expression plasmid has several advantages in high level heterologous expression systems. The desired cDNA insert is ligated in frame to plasmid vector sequences encoding six histidines followed by a highly specific protease recognition site (thrombin) that are joined to the amino terminus codon of the target protein. The histidine "block"

of the expressed fusion protein promotes very tight binding to immobilized metal ions and permits rapid purification of the recombinant protein by immobilized metal ion affinity chromatography. The histidine leader sequence is then cleaved at the specific proteolysis site by treatment of the purified protein with thrombin, and the geranyl diphosphate synthase again purified by immobilized metal ion affinity chromatography, this time using a shallower imidazole gradient to elute the recombinant synthase while leaving the histidine block still adsorbed. This overexpression-purification system has high capacity, excellent resolving power and is fast, and the chance of a contaminating E. coli protein exhibiting similar binding behavior (before and after thrombin proteolysis) is extremely small.

As will be apparent to those skilled in the art, any plasmid vectors containing replicon and control sequences that are derived from species compatible with the host cell may also be used in the practice of the invention. The vector usually has a replication site, marker genes that provide phenotypic selection in transformed cells, one or more promoters, and a polylinker region containing several restriction sites for insertion of foreign DNA. Plasmids typically used for transformation of E. coli include pBR322, pUC18, pUC19, pUCl18, pUC119, and Bluescript M13, all of which are described in sections 1.12–1.20 of Sambrook et al., supra. However, many other suitable vectors are available as well. These vectors contain genes coding for ampicillin and/or tetracycline resistance which enables cells transformed with these vectors to grow in the presence of these antibiotics.

The promoters most commonly used in prokaryotic vectors include the β-lactamase (penicillinase) and lactose promoter systems (Chang et al. *Nature* 375:615 [1978]; Itakura et al., *Science* 198:1056 [1977]; Goeddel et al., *Nature* 281:544 [1979]) and a tryptophan (trp) promoter system (Goeddel et al., *Nucl. Acids Res.* 8:4057 [1980]; EPO Appl. Publ. No. 36,776), and the alkaline phosphatase systems. While these are the most commonly used, other microbial promoters have been utilized, and details concerning their nucleotide sequences have been published, enabling a skilled worker to ligate them functionally into plasmid vectors (see Siebenlist et al., *Cell* 20:269 [1980]).

Many eukaryotic proteins normally secreted from the cell contain an endogenous secretion signal sequence as part of the amino acid sequence. Thus, proteins normally found in the cytoplasm can be targeted for secretion by linking a signal sequence to the protein. This is readily accomplished by ligating DNA encoding a signal sequence to the 5' end of the DNA encoding the protein and then expressing this fusion protein in an appropriate host cell. The DNA encoding the signal sequence may be obtained as a restriction fragment from any gene encoding a protein with a signal sequence. Thus, prokaryotic, yeast, and eukaryotic signal sequences may be used herein, depending on the type of host cell utilized to practice the invention. The DNA and amino acid sequence encoding the signal sequence portion of several eukaryotic genes including, for example, human growth hormone, proinsulin, and proalbumin are known (see Stryer, *Biochemisty* W. H. Freeman and Company, New York, N.Y., p. 769 [1988]), and can be used as signal sequences in appropriate eukaryotic host cells. Yeast signal sequences, as for example acid phosphatase (Arima et al., *Nuc. Acids Res.* 11:1657 [1983]), alpha-factor, alkaline phosphatase and invertase may be used to direct secretion from yeast host cells. Prokaryotic signal sequences from genes encoding, for example, LamB or OmpF (Wong et al., *Gene* 68:193 [1988]), MalE, PhoA, or beta-lactamase, as well as other genes, may be used to target proteins from prokaryotic cells into the culture medium.

As described at pages 17–18, supra, the geranyl diphosphate synthase amino terminal membrane insertion sequence resides at SEQ ID No:2, residues 1 through 48, and in the embodiment shown in SEQ ID No:2 directs the enzyme to plastids. Alternative trafficking sequences from plants, animals and microbes can be employed in the practice of the invention to direct the gene product to the cytoplasm, endoplasmic reticulum, mitochondria or other cellular components, or to target the protein for export to the medium. These considerations apply to the overexpression of geranyl diphosphate synthase, and to direction of expression within cells or intact organisms to permit gene product function in any desired location.

The construction of suitable vectors containing DNA encoding replication sequences, regulatory sequences, phenotypic selection genes and the geranyl diphosphate synthase DNA of interest are prepared using standard recombinant DNA procedures. Isolated plasmids and DNA fragments are cleaved, tailored, and ligated together in a specific order to generate the desired vectors, as is well known in the art (see, for example, Sambrook et al., supra).

As discussed above, geranyl diphosphate synthase variants are preferably produced by means of mutation(s) that are generated using the method of site-specific mutagenesis. This method requires the synthesis and use of specific oligonucleotides that encode both the sequence of the desired mutation and a sufficient number of adjacent nucleotides to allow the oligonucleotide to stably hybridize to the DNA template.

In another aspect of the invention, the gene encoding geranyl diphosphate synthase may be introduced into cancerous cells in combination with a gene encoding a monoterpene synthase that produces a monoterpene having anti-cancer properties. A geranyl diphosphate synthase gene must be introduced into cancerous cells, in addition to a gene encoding a monoterpene synthase producing a monoterpene having anti-cancer properties, because animal cells do not naturally produce geranyl diphosphate which is the chemical precursor to the monoterpenes. Examples of monoterpenes having anti-cancer properties are limonene, perillyl alcohol and geraniol, as discussed at page 4, supra.

Several methods are known in the art for the introduction of genes into human cells. For example, cell-based therapy can be used to introduce genes into cells while they are outside of the body. Cell-based approaches involve removing cells from a patient, introducing genes encoding a therapeutic protein into the removed cells, and returning the cells to the patient by cell transplantation or transfusion. The cell-based approach has been used to treat Severe Combined Immune Deficiency (SCID), which is due to inherited defects in the enzyme adenosine deaminase (ADA). The gene therapy treatment of SCID involved removal of peripheral blood lymphocytes or bone marrow progenitor cells from affected individuals, introduction of the normal ADA gene into the chromosomes of these cells using retroviral vectors, and reintroduction of the genetically engineered cells to the patient (C. Bordignon et al. *Science* 270:470, 474 (1995), R. M. Blaese et al., *Science* 270:475–479 (1995); D. B. Kohn et al., *Nature Med.* 1: 1017–1023 (1995)). Initial results demonstrated that the genetically engineered cells will persist for prolonged periods of time, and that low level expression of ADA can be established.

Analogous cell-based approaches have been used to treat familial hypercholesterolemia (LDL-receptor deficiency) (M. Grossman et al., *Nature Genetics* 6:335 41 (1994); M. Grossman et al., *Nature Med* 1:1148–1154 (1995)) and Gaucher disease (J. A. Nolta et al., *J. Clin. Invest.* 90:342–348 (1992); L. Xu et al., *Exptl. Hematol.* 22:223–230 (1994); T. Ohashi et al., *Proc. Natl. Acad. Sci. USA.* 89:11332–11336 (1992)).

Genes can be introduced into cells in situ, or after removal of the cells from the body, by means of viral vectors. For example, retroviruses are RNA viruses that have the ability to insert their genes into host cell chromosomes after infection. Retroviral vectors have been developed that lack the genes encoding viral proteins, but retain the ability to infect cells and insert their genes into the chromosomes of the target cell (A. D. Miller, *Hum. Gen. Ther.* 1:5–14 (1990)). Retroviruses will only efficiently infect dividing cells, thus when retroviruses are used to introduce genes into cells that have been removed from the body, cell division is stimulated with growth-promoting media or specific factors. In vivo application of retroviruses has been achieved by administration of virus-producing cells directly into tumors. Virus particle released by the infected cell will infect adjacent tumor cells, hence only a relatively small percentage of cells in a tumor need be initially infected in order to ultimately introduce the targeted gene into most or all of the tumor cells. (K. W. Culver et al., *Science* 256:1550–1552 (1992)).

Adenoviral vectors are designed to be administered directly to patients. Unlike retroviral vectors, adenoviral vectors do not integrate into the chromosome of the host cell. Instead, genes introduced into cells using adenoviral vectors are maintained in the nucleus as an extrachromosomal element (episome) that persists for a limited time period. Adenoviral vectors will infect dividing and non-dividing cells in many different tissues in vivo including airway epithelial cells, endothelial cells, hepatocytes and various tumors (B. C. Trapnell, *Adv Drug Del Rev.* 12:185–199 (1993)).

Another viral vector is the herpes simplex virus, a large, double-stranded DNA virus that has been used in some initial applications to deliver therapeutic genes to neurons and could potentially be used to deliver therapeutic genes to some forms of brain cancer (D. S. Latchman, *Mol. Biotechnol.* 2:179–95 (1994)). Recombinant forms of the vaccinia virus can accommodate large inserts and are generated by homologous recombination. To date, this vector has been used to deliver interleukins (ILs), such as human IL-1β and the costimulatory molecules B7-1 and B7-2 (G. R. Peplinski et al., *Ann. Surg. Oncol.* 2:151–9 (1995); J. W. Hodge et al., *Cancer Res.* 54:5552–55 (1994)).

Another approach to gene therapy involves the direct introduction of DNA plasmids into patients. (F. D. Ledley, *Hum. Gene Ther.* 6:1129–1144 (1995)). The plasmid DNA is taken up by cells within the body and can direct expression of recombinant proteins. Typically plasmid DNA is delivered to cells in the form of liposomes in which the DNA is associated with one or more lipids, such as DOTMA (1,2,-diolcyloxypropyl-3-trimethyl ammonium bromide) and DOPE (dioleoylphosphatidylethanolamine). Formulations with DOTMA have been shown to provide expression in pulmonary epithelial cells in animal models (K. L. Brigham et al., *Am. J. Med. Sci,* 298:278–281 (1989); A. B. Canonico et al., *Am. J. Respir. Cell. Mol. Biol.* 10:24–29 (1994)). Additionally, studies have demonstrated that intramuscular injection of plasmid DNA formulated with 5% PVP (50,000 kDa) increases the level of reporter gene expression in muscle as much as 200-fold over the levels found with injection of DNA in saline alone (R. J. Mumper et al., *Pharm. Res.* 13:701–709 (1996); R. J. Mumper et al., *Proc. Intern. Symp. Cont. Rol. Bioac. Mater.* 22:325–326 (1995)). Intramuscular administration of plasmid DNA results in gene expression that lasts for many months (J. A. Wolff et al., *Hum. Mol. Genet.* 1:363–369 (1992); M. Manthorpe et al., *Hum. Gene Ther.* 4:419–431 (1993); G. Ascadi et al., *New Biol.* 3:71–81 (1991), D. Gal et al., *Lab. Invest.* 68:18–25 (1993)).

Additionally, uptake and expression of DNA has also been observed after direct injection of plasmid into the thyroid (M. Sikes et al., *Hum. Gene Ther.* 5:837–844 (1994)) and synovium (J. Yovandich et al., *Hum. Gene Ther.* 6:603–610 (1995)). Lower levels of gene expression have been observed after interstitial injection into liver (M. A. Hickman et al., *Hum. Gene Ther.* 5:1477–1483 (1994)), skin (E. Raz et al., *Proc. Natl. Acad. Sci.* 91:9519–9523 (1994)), instillation into the airways (K. B. Meyer et al., *Gene Therapy* 2:450–460 (1995)), application to the endothelium (G. D. Chapman et al., *Circulation Res.* 71:27–33 (1992); R. Riessen et al., *Human Gene Therapy,* 4:749–758 (1993)), and after intravenous administration (R. M. Conry et al., *Cancer Res.* 54:1164–1168 (1994)).

Various devices have been developed for enhancing the availability of DNA to the target cell. A simple approach is to contact the target cell physically with catheters or implantable materials containing DNA (G. D. Chapman et al., *Circulation Res.* 71:27–33 (1992)). Another approach is to utilize needle-free, jet injection devices which project a column of liquid directly into the target tissue under high pressure. (P. A. Furth et al., *Anal Biochem.* 20:365–368 (1992); (H. L. Vahlsing et al., *J. Immunol. Meth.* 175:11–22 (1994); (F. D. Ledley et al., *Cell Biochem.* 18A:226 (1994)).

Another device for gene delivery is the "gene gun" or Biolistic™, a ballistic device that projects DNA-coated micro-particles directly into the nucleus of cells in vivo. Once within the nucleus, the DNA dissolves from the gold or tungsten microparticle and can be expressed by the target cell. This method has been used effectively to transfer genes directly into the skin, liver and muscle (N. S. Yang et al., *Proc. Natl. Acad. Sci.* 87:9568–9572 (1990); L. Cheng et al., *Proc. Natl. Acad. Sci. USA.* 90:4455–4459 (1993); R. S. Williams et al., *Proc. Nail. Acad. Sci.* 88:2726–2730 (1991) ).

Another approach to targeted gene delivery is the use of molecular conjugates, which consist of protein or synthetic ligands to which a nucleic acid- or DNA-binding agent has been attached for the specific targeting of nucleic acids to cells (R. J. Cristiano et al., *Proc. Natl. Acad. Sci. USA* 90:11548–52 (1993); B. A. Bunnell et al., *Somat. Call Mol. Genet.* 18:559–69 (1992); M. Cotten et al., *Proc. Natl. Acad. Sci. USA* 89:6094–98 (1992)). Once the DNA is coupled to the molecular conjugate, a protein-DNA complex results. This gene delivery system has been shown to be capable of targeted delivery to many cell types through the use of different ligands (R. J. Cristiano et al., *Proc. Natl. Acad. Sci. USA* 90:11548–52 (1993)). For example, the vitamin folate has been used as a ligand to promote delivery of plasmid DNA into cells that overexpress the folate receptor (e.g., ovarian carcinoma cells) (S. Gottschalk et.,al., *Gene Ther.* 1:185–91 (1994)). The malaria circumsporozoite protein has been used for the liver-specific delivery of genes under conditions in which ASOR receptor expression on hepatocytes is low, such as in cirrhosis, diabetes, and hepatocellular carcinoma (Z. Ding et al., *J. Biol. Chem.* 270:3667–76 (1995)). The overexpression of receptors for epidermal growth factor (EGF) on cancer cells has allowed for specific uptake of EGF/DNA complexes by lung cancer cells (R. Cristiano et al., *Cancer Gene Ther.* 3:4–10 (1996)).

Targeted expression of genes encoding proteins having anti-cancer activity can be achieved by placing the transgene under the control of an inducible promoter. For example, the promoter for the carcinoembryonic antigen (CEA) gene has been incorporated in vectors and it has directed cell-specific expression of the resulting CEA-expression vector constructs in tumors cells, such as those of pancreatic carcinoma (J. M. DiMaio et al., *Surgery* 116:205–13 (1994)). The regulatory sequences of the human surfactant protein A gene have been used to generate cell-specific expression in non-small-cell lung cancers that express this protein (M. J. Smith et al., *Hum. Gene Ther.* 5:29–35 (1994)).

Another approach to introducing geranyl diphosphate synthase protein, and monoterpene synthase protein, into a cancerous cell is to directly introduce the purified protein into the body. Typically, the protein is introduced in association with another molecule, such as a lipid, to protect the protein from enzymatic degradation. For example, the covalent attachment of polymers, especially polyethylene glycol (PEG), has been used to protect certain proteins from enzymatic hydrolysis in the body and thus prolong half-life (F. Fuertges, et al., *J. Controlled Release,* 11:139 (1990)). Many polymer systems have been reported for protein delivery (Y. H. Bae, et al., *J. Controlled Release,* 9:271 (1989); R. Hori, et al., *Pharm. Res.,* 6:813 (1989); I. Yamakawa, et al., *J. Pharm. Sci.,* 79:505 (1990); I. Yoshihiro, et al., *J. Controlled Release,* 10:195 (1989); M. Asano, et al., *J. Controlled Release,* 9:111 (1989); J. Rosenblatt et al., *J. Controlled Release,* 9:195 (1989); K. Makino, *J. Controlled Release,* 12:235 (1990); Y. Takakura et al., *J. Pharm. Sci.,* 78:117 (1989); Y. Takakura et al., *J. Pharm. Sci.,* 78:219 (1989)).

Therapeutic proteins can be introduced into the body by application to a bodily membrane capable of absorbing the protein, for example the nasal, gastrointestinal and rectal membranes. The protein is typically applied to the absorptive membrane in conjunction with a permeation enhancer. (V. H. L. Lee, *Crit. Rev. Ther. Drug Carrier Syst.,* 5:69 (1988); V. H. L. Lee, *J. Controlled Release,* 13:213 (1990); V. H. L. Lee, Ed., *Peptide and Protein Drug Delivery,* Marcel Dekker, New York (1991); A. G. DeBoer et al., *J. Controlled Release,* 13:241 (1990)). For example, STDHF is a synthetic derivative of fusidic acid, a steroidal surfactant that is similar in structure to the bile salts, and has been used as a permeation enhancer for nasal delivery. (W. A. Lee, *Biopharm.* Nov./Dec., 22, 1990).

Additionally, microspheres bearing therapeutic protein can be delivered to the body. In one application, a bioadhesive was used to hold microspheres bearing protein in place in the nasal passages. When an absorption enhancer was incorporated into the microsphere with the protein, bioavailability was increased (L. Illum, et al., *Int. J. Pharm.,* 63:207 (1990); N. F. Farraj et al., *J. Controlled Release,* 13:253 (1990)).

The foregoing may be more fully understood in connection with the following representative examples, in which "Plasmids" are designated by a lower case p followed by an alphanumeric designation. The starting plasmids used in this invention are either commercially available, publicly available on an unrestricted basis, or can be constructed from such available plasmids using published procedures. In addition, other equivalent plasmids are known in the art and will be apparent to the ordinary artisan.

"Digestion", "cutting" or "cleaving" of DNA refers to catalytic cleavage of the DNA with an enzyme that acts only at particular locations in the DNA. These enzymes are called restriction endonucleases, and the site along the DNA sequence where each enzyme cleaves is called a restriction site. The restriction enzymes used in this invention are commercially available and are used according to the instructions supplied by the manufacturers. (See also sections 1.60–1.61 and sections 3.38–3.39 of Sambrook et al., supra.)

"Recovery" or "isolation" of a given fragment of DNA from a restriction digest means separation of the resulting DNA fragment on a polyacrylamide or an agarose gel by electrophoresis, identification of the fragment of interest by comparison of its mobility versus that of marker DNA fragments of known molecular weight, removal of the gel section containing the desired fragment, and separation of the gel from DNA. This procedure is known generally. For example, see Lawn et al. (*Nucleic Acids Res.* 9:6103–6114 (1982)), and Goeddel et al. (*Nucleic Acids Res.,* supra).

The following examples merely illustrate the best mode now contemplated for practicing the invention, but should not be construed to limit the invention. All literature citations herein are expressly incorporated by reference.

EXAMPLES

Example 1

Geranyl Diphosphate Synthase Isolation

The purification strategy for Mentha geranyl diphosphate synthase was developed empirically. The teachings of the prior art were inconsistent and could not be adapted for use in the isolation of geranyl diphosphate synthase from Mentha. For example, Clastre et al, supra, provides the only example in the art of completely purified geranyl diphosphate synthase (from grape). The purification protocol of Clastre et al consisted of the following steps: ammonium sulfate precipitation, anion exchange chromatography (DEAE and Mono Q), hydroxyapatite chromatography, hydrophobic (phenyl-substituted) chromatography, gel permeation chromatography and non-denaturing polyacrylamide gel electrophoresis. Clastre et al reported that ammonium sulfate precipitation was the most efficient purification step. In contrast, in the purification of Mentha geranyl diphosphate synthase, reported herein, the techniques of ammonium sulfate precipitation, hydroxyapatite chromatography, hydrophobic (phenyl-substituted) chromatography and gel permeation chromatography all failed. In particular, ammonium sulfate precipitation was particularly inefficient when applied to the isolation of Mentha geranyl diphosphate synthase. Consequently, the following purification protocol was developed empirically.

Plant materials, substrates and reagents. Mint plants (*Mentha spicata*) were propagated and grown as previously described (Alonso et al., *J. Biol. Chem.* 267:7582–7587, 1992). Newly emerged, rapidly expanding leaves (5–10 mm long) of vegetative stems (3–7 weeks old) were used for the preparation of glandular trichome cells for enzyme purification (Gershenzon et al., *Anal. Biochem.* 200:130–138, 1992). [4-$^{14}$C]Isopentenyl diphosphate (54 Ci/mol) was purchased from DuPont/NEN. Dimethylallyl diphosphate was synthesized as described (Davisson et al., *Methods Enzymol* 110:130–144, 1985).

Assay for prenyltransferase activity. To 10 µl of enzyme solution was added 90 µl MOPSO buffer (25 mM, pH 7.0) containing 10% glycerol, 10 mM MgCl$_2$, and 1 mM DTT. DMAPP (10 µM) and [4-$^{14}$C]IPP (7 µM) were added to initiate the reaction, and the contents were overlaid with 1 ml hexane. The mixture was vortexed briefly and then incubated for 1 h at 31° C. After incubation, 10 µl of 3N HCl was added, the contents vortexed and centrifuged, and hydrolysis of the products was continued for 20 min at 31° C. After hydrolysis was complete, the reaction mixture was again vortexed and centrifuged so that the products derived from the acid labile allylic diphosphates (or those alcohols derived from hydrolysis by endogenous phosphatases) were partitioned into the hexane layer. The hexane was removed and the radioactive products contained therein were measured by liquid scintillation counting.

Product identification. For the identification of reaction products, the assay was scaled up by a factor of ten and pentane was substituted for the hexane overlay to improve recovery. After acid hydrolysis and removal of the pentane layer as described above, the reaction mixture was extracted with 2×1 ml of diethyl ether to ensure complete recovery of products. The combined organic extract was then dried over anhydrous $Na_2SO_4$ and concentrated to 100 µl, followed by addition of internal standards and further concentration for radio-GLC analysis. The products sought were: from farnesyl diphosphate, all trans-farnesol from endogenous phosphatase-catalyzed hydrolysis and cis,trans-farnesol and nerolidol from acid-catalyzed rearrangement (total $C_{15}$ alcohols); from geranyl diphosphate, geraniol from endogenous phosphatase-catalyzed hydrolysis and nerol and linalool from acid-catalyzed rearrangement (total $C_{10}$ alcohols); and total $C_5$ alcohols (dimethylallyl alcohol, isopentenol and dimethylvinyl carbinol).

Initial Preparation of Mint Glandular Trichome Extract Containing Geranyl Diphosphate Synthase. Glandular trichome cell clusters (approximately $2 \times 10^7$) were isolated from 40 g of leaf tissue following procedures previously described (Gershenzon et al., *Anal. Biochem.* 200:130–138, 1992). The isolated cell clusters were suspended in KPi buffer (50 ml, 100 mM, pH 7.4, containing 5 g XAD, 0.5 g PVPP, 250 mM sucrose, 1 mM DTT, 1 mM PMSF and 1 mM $Na_4EDTA$), and were disrupted by sonication (Braun-sonic 2000, full power, five 15 s bursts separated by 45 s cooling in ice). The sonicate was filtered through a 20 µm nylon mesh and the filtrate was brought to 100 ml by the addition of 50 ml KPi buffer without XAD or PVPP. The sonicate was then centrifuged at 18,000 g (30 min), then at 195,000g (90 min), and the supernatant was utilized as the enzyme source.

Dye-ligand interaction chromatography. The supernatant combined from two gland preparations (200 ml) was dialyzed (2×, 4° C., 18 h total) in Mes buffer (4 l, 25 mM, pH 6.2) containing 10% glycerol, 1 mM DTT, and 10 mM $MgCl_2$. The dialyzed supernatant was equally divided into 8 (50 ml) polypropylene tubes containing 5 ml of DyeMatrex Red A Gel (Amicon) equilibrated with dialysis buffer in each tube. After 1 h of gentle mixing (Labquake), the contents were poured into eight 1.5×12 cm polypropylene columns (Bio-Rad), gravity drained, and washed with 4× volumes of dialysis buffer. Geranyl diphosphate synthase was then eluted with Bis-Tris buffer (240 ml, 25 mM, pH 7.0) containing 10% glycerol, 5 mM KPi, 1 mM DTT, and 1 mM EDTA. The entire procedure was performed at 0°–4° C.

Anion exchange chromatography. The elutant from the dye-ligand interaction chromatography step was loaded on to an HR 10/10 column containing Source 15Q separation media (Pharmacia Biotech) equilibrated in Bis-Tris buffer A (25 mM, pH 7.0) containing 10% glycerol and 1 mM DTT. Geranyl diphosphate synthase was eluted with a gradient (0–400 mM KCl in buffer A; total volume 400 ml). The highest activity fractions were collected (6 ml) and stored at −80° C. Farnesyl diphosphate synthase eluted at 4–10 mM KCl; geranyl diphosphate synthase eluted at 140–180 mM KCl; geranylgeranyl diphosphate synthase activity was not detected. Anion exchange chromatography afforded the most significant purification step for geranyl diphosphate synthase.

To identify the geranyl diphosphate synthase protein in the anion exchange chromatography fractions, equal volumes from each fraction containing geranyl diphosphate activity were loaded onto an SDS-PAGE gel and the proteins contained therein were resolved and silver stained. The correlation of protein stain intensity with geranyl diphosphate synthase activity level in each fraction allowed the identification of a well resolved 29 kDa band as the target enzyme. Additional evidence was provided by calibrated gel permeation chromatography (Superdex 75) which indicated that the geranyl diphosphate synthase eluted at volumes corresponding to ~70 kDa (major) and ~30 kDa, consistent with a 70 kDa homodimeric native enzyme that yields 30 kDa subunits which retain at least some catalytic activity.

Preparative SDS-PAGE. The partially purified geranyl diphosphate synthase from the anion chromatography step (60 ml) was heated to 95° C. for 15 min, cooled, and dialyzed in distilled water (2×, 4 l, 18 h, 4° C.). The protein solution was then lyophilized to a powder and suspended in 100 µl of SDS buffer plus 50 µl of 3× loading buffer and separated by SDS-PAGE on 12.5% acrylamide at 35 mA for 6 h [15 cm×18 cm×1.5 mm gel] by a standard protocol (Laemmli, U. K., *Nature* 227:680–685, 1970). Coomassie Blue staining revealed ten protein bands, with the most prominent band corresponding to 29 kDa and estimated at 10µg protein, based upon calibrated staining intensity with carbonic anhydrase as reference. The 29 kDa protein band, that was coincident with geranyl diphosphate synthase activity on ion exchange chromatography, was excised from the gel and combined in a microcentrifuge tube.

Amino acid analysis and protein sequencing. The presumptive geranyl diphosphate synthase protein (approximately 10 µg) contained in the SDS-PAGE gel slice was digested with trypsin (Promega V511/1,2) following published protocols (Coligan, J. E. in Coligan et al., eds. "Current Protocols in Protein Science, Vol. 1," John Wiley and Sons, New York, 11.3.1–11.3.13, 1996). The peptide mixture was then loaded onto an Applied Biosystems C18 column (Aquapure ODS-300) which was equilibrated with distilled water/1% trifluoroacetic acid (TFA) (buffer A) and separated by gradient elution with buffer B consisting of 70% $CH_3CN$, 29% distilled water, and 1% TFA (0–60 min, 0%–37% buffer B/60–90 min, 37%–75% buffer B/ 90–105 min, 75%–100% buffer B). Five resolvable peptides were subjected to amino-terminal sequence analysis via Edman degradation at the Washington State University Laboratory for Biotechnology and Bioanalysis. Two of the five digestion products yielded unambiguous peptide sequences; FGLYQGTLR (SEQ ID No:3) and RVIIEISR (SEQ ID No:7). The other peptides collected yielded no useful sequence information, either because of low recovery or due to the presence of contaminants.

Example 2

Cloning of Geranyl Diphosphate Synthase cDNA

Shotgun cloning and sequencing. Since further scale-up of the geranyl diphosphate synthase purification protocol was impractical, the limited geranyl diphosphate synthase peptide sequence information precluded an exclusively sequence-based cloning strategy. Consequently, a random sequencing effort was initiated from a highly enriched source, i.e., a cDNA library constructed from mRNA isolated from peppermint oil gland cells that constitute the exclusive source of monoterpene biosynthesis in Mentha.

Mint plants (*Mentha piperita*) were propagated and grown as previously described (Alonso et al., *J. Biol. Chem.* 267:7582–7587, 1992). Secretory cells were isolated from 5-day-old peppermint leaves (Gershenzon et al., *Anal. Biochem.* 200:130–138, 1992), and total RNA was extracted from the isolated secretory cells (Logemann et al., *Anal. Biochem.* 163: 16–20, 1987). Poly(A)$^+$-RNA was purified by chromatography on oligo(dT)-cellulose (Pharmacia), and 5 μg of the resulting mRNA were utilized to construct a λZAP cDNA library according to the manufacturer's instructions (Stratagene). Plasmids were purified from a mass excision of mint gland λZAPII phagemids (Stratagene). The plasmids were sequenced (DyeDeoxy Terminator Cycle Sequencing, Applied Biosystems) using the T3 promoter primer and the data subsequently acquired on the ABI sequenator. The NCBI BLAST server was used for database searching using the programs of the GCG Wisconsin package (Genetics Computer Group. 1994 Program Manual for the Wisconsin Package, Version 8, Genetics Computer Group, Madison, Wis.).

Within the first one hundred clones sequenced, one promising clone (Mp10:13) was found to be "prenyltransferase-like" in sequence, in that it showed low homology to plant-derived geranylgeranyl diphosphate synthases (~28% identity; ~54% similarity) but little homology to plant-derived farnesyl diphosphate synthases (~16% identity; ~40% similarity). The PCR primers pMp13F (SEQ ID No:4) and pMp13R (SEQ ID No:5), derived from the sequence of clone Mp10:13, were used to amplify a 113 bp, 5'-fragment (SEQ ID No:6) which was labeled using the same primers and $\alpha^{32}$P-dATP. The resulting probe was used to screen 3000 mint gland library αZAPII cDNA clones at high stringency. The filters bearing the 3000 αZAPII cDNA clones were hybridized with the radiolabelled, 113 bp probe overnight at 42° C. in 30% formaldehyde, 5X SSPE (0.75M NaCl, 0.05M NaH$_2$PO$_4$, 0.005M EDTA at pH 7.4), 5× Denhardts Reagent (0.1% Ficoll 400, 0.1% polyvinylpyrrolidone, 0.1% bovine serum albumin), 0.1% SDS and 20 μg/ml denatured, sheared herring sperm DNA. The filters were then washed three times, for thirty minutes per wash, in 1× SSC (0.1SM NaCl and 0.0165M sodium citrate) and 0.1% SDS at 65° C. Twenty-seven positive clones were purified through a second round of screening and were sequenced with T3 and T7 promoter primers. Sequencing revealed that the cloned genes represented three alleles.

Assay of the Biological Activity of the Proteins Encoded by the Putative Geranyl Diphosphate Synthase cDNAs. One full-length, in-frame clone from each putative geranyl diphosphate synthase allele was transformed into *E. coli* XL1-Blue and was grown to OD$_{600}$=0.7, induced with 1 mM IPTG and allowed to express for 6 h at 20° C. The bacteria were harvested by centrifugation, resuspended in assay buffer, and disrupted by brief sonication. The extract was cleared of debris by centrifugation and the resulting supernatant assayed using $^{14}$C-IPP and DMAPP as cosubstrates as described in Example 1, except that 1 mM PMSF, 1 mM EDTA and 0.1% Triton X-100 were included in the incubation mixture. One of the clones, designated Mp13.18, was shown to have the highest level of expressed activity and the cDNA insert was sequenced completely on both strands (SEQ ID No:1).

Plants employ different codon usage than *E. coli* and the presence of arginine codons AGA and AGG can lead to mistranslation or truncation of eukaryotic proteins when heterologously expressed in *E. coli*. Since nine of the 14 arginines in the clone Mp13.18 sequence are coded for by these rare *E. coli* tRNAs, the pET3a-derived vector, pSBETa, was chosen for expression. This vector, in addition to driving expression with T7 DNA polymerase from the strong T7lac promoter, carries the sequence encoding the tRNA for rare arginine codon usage (Schenk et al., *BioTechniques* 19:196–200, 1995).

To clone the open reading frame of Mp13.18 directionally into pSBETa, an NdeI site (CAT ATG) was added at the starting methionine by site directed mutagenesis (QuickChange, Stratagene), and a convenient BamHI site (8 bp downstream of the stop codon) was utilized. The vector and engineered derivative of Mp13.18, designated Mp13.18N, were double digested with BamHI and NdeI, the fragments were gel purified and ligated overnight, and then transformed into *E. coli* XL1-Blue competent cells. The resulting plasmid, designated pSB13.18, was purified, sequenced to verify that no undesired changes occurred during mutagenesis, and transformed into the T7 expression strain, *E. coli* BL21(DE3)pLysS. Clone pSB13.18 was used in all subsequent studies of geranyl diphosphate synthase expression in *E. coli*. Expression in *E. coli* was performed as described above.

Confirmation of the identity of the putative GPP synthase encoded by plasmid Mp13.18 using the GPP synthase peptide amino acid sequence information. Functional expression of a putative geranyl diphosphate synthase gene in *E. coli* does not absolutely prove that the cloned cDNA encodes geranyl diphosphate synthase. Functional expression of GPP synthase is complicated by the fact that the host cells used in all expression systems (plant, microbial and animal) contain competing phosphatases that can hydrolyse both the substrates (dimethylallyl diphosphate and isopentenyl diphosphate) and the product (geranyl diphosphate) of the reaction catalyzed by GPP synthase. Consequently, there exists the possibility of false negative results in cell-free extracts of the recombinant enzyme.

Additionally, functional expression is complicated by the fact that all host cells (plant, microbial and animal) contain endogenous FPP synthase. This enzyme synthesizes GPP ($C_{10}$) on route to the $C_{15}$ homolog farnesyl diphosphate (see FIG. 1), and it is known in the art that mutated, altered or otherwise degraded forms of FPP synthase (generated for example by cell breakage in the process of cell-free assay of the recombinant enzyme) will release the geranyl diphosphate intermediate, thus leading to a false positive indication of the presence of GPP synthase (Wise, M. L. and Croteau, R., in Cane, D. E., ed., "Comprehensive Natural Products Chemistry: Isoprenoids, Vol. 2" Elsevier Science, Oxford, 1997 (in press); Ogura, K. and Koyama, T., in Ogura, K. and Sankawa, U., eds., "Dynamic Aspects of Natural Products Chemistry" Kodansha/Harwood Academic Publishers, Tokyo, pp. 1–23, 1997). Such artefactual formation of GPP is observed in *E. coli* extracts and so extreme care and reproducibility, and the use of controls in each case, are required in monitoring recombinant enzyme activity.

Finally, one of the substrates of the reaction (dimethylallyl diphosphate) can displace the bound geranyl diphosphate intermediate of the FPP synthase enzyme, and so even minor alterations in the assay or reaction medium can give rise to false positive indications for the presence of GPP synthase. The assay described herein was designed to minimize this complication, but this kinetic effect is highly variable and dependent on conditions of the medium. Thus, there are severe complications with functional heterologous expression of GPP synthase, primarily leading to false positives, that prevent reliance on functional expression as a means of confirming clone identity. For this reason, and in spite of positive indication by functional expression, the GPP synthase clone could be unambiguously confirmed only by matching the limited available GPP synthase amino acid sequence data from the purified protein to the amino acid sequence data derived from the putative geranyl diphosphate synthase cDNA.

Alignment of the two peptide sequences derived from purified GPP synthase (SEQ ID No:3 and SEQ ID No:7) with the deduced amino acid sequence of putative GPP synthase clone Mp 13.18 (SEQ ID No:2) revealed that the nine amino acid peptide (SEQ. ID No:3) exactly corresponded to amino acid residues 254 to 262 of the putative GPP synthase sequence (SEQ ID No:2), while the eight amino acid peptide (SEQ ID No:7) exactly corresponded to amino acid residues 184 to 191 of the putative GPP synthase sequence (SEQ ID No:2).

Example 3

Sequence Analysis of Geranyl Diphosphate Synthase cDNA Insert of Plasmid Mp13.18

The geranyl diphosphate synthase clone encoded by the cDNA insert of Mp13.18 (1131 nt), which yielded the highest expressed level of synthase activity, contained an open reading frame of 939 nucleotides, corresponding to a protein of 313 amino acids with a calculated molecular weight of 33,465. The first 48 deduced amino acid residues show the expected characteristics of a plastidial targeting sequence, i.e., the sequence is rich in serine residues and amino acid residues with small, hydrophobic side chains, and is low in acidic residues (von Heijne et al., *Eur. J. Biochem.* 180:535–545, 1989). The presence of a putative, amino-terminal targeting sequence is consistent with the plastidial origin of monoterpene biosynthesis in plant cells (Wise, M. L. and Croteau, R., in Cane, D. E., ed., "Comprehensive Natural Products Chemistry: Isoprenoids, Vol. 2" Elsevier Science, Oxford, 1997 (in press). By excluding the putative transit peptide residues, the amino acid sequence corresponds to a mature, processed protein of molecular weight 28,485, in full agreement with a molecular weight of about 29,000 (monomeric subunit size) determined for the native enzyme by SDS-PAGE.

An alignment of translated, plant-derived prenyltransferase sequences reveals a closer relationship between the Mentha geranyl diphosphate synthase and plant geranylgeranyl diphosphate synthases (~28% identity; ~54% similarity), than between the Mentha geranyl diphosphate synthase and plant farnesyl diphosphate synthases (~16% identity; ~40% similarity). The observation that the Mentha geranyl diphosphate synthase is more closely related to geranylgeranyl diphosphate synthases than to farnesyl diphosphate synthases is consistent with the plastidial location of geranyl diphosphate synthase and geranylgeranyl diphosphate synthases, unlike farnesyl diphosphate synthases which are located in the cytoplasm. Although the Mentha geranyl diphosphate synthase is more closely related to geranylgeranyl diphosphate synthases than to farnesyl diphosphate synthases, it is nonetheless apparent that there is low overall identity and similarity between the Mentha geranyl diphosphate synthase and either geranylgeranyl diphosphate synthases or farnesyl diphosphate synthases.

The embodiments of the invention in which an exclusive property or privilege is claimed are defined as follows:

1. An isolated nucleotide sequence encoding geranyl diphosphate synthase from a Mentha species.

2. A nucleotide sequence of claim 1 encoding geranyl diphosphate synthase from *Mentha piperita*.

3. An isolated nucleotide sequence encoding a Mentha protein having the biological activity of SEQ. ID. No:2.

4. An isolated nucleotide sequence of claim 3 which encodes the amino acid sequence of SEQ. ID. No:2.

5. An isolated nucleotide sequence of claim 3 consisting of the sequence of SEQ. ID. No:1.

6. A replicable expression vector comprising a nucleotide sequence encoding a protein having the biological activity of SEQ. ID. No:2.

7. A replicable expression vector of claim 6 wherein the nucleotide sequence comprises the sequence of SEQ. ID. No:1.

8. A host cell comprising the vector of claim 6.

9. A method of enhancing the production of geranyl diphosphate synthase in a host cell comprising introducing into the host cell an expression vector of claim 6 encoding a protein having the biological activity of SEQ. ID. No:2 under conditions enabling expression of the protein in the host cell.

10. A method of claim 9 wherein the host cell is a eukaryotic cell.

11. A method of claim 10 wherein the host cell is a plant cell.

12. A method of claim 10 wherein the host cell is an animal cell.

* * * * *

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 1131 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Mentha piperita ( v i i ) IMMEDIATE SOURCE:
        ( B ) CLONE: Mint geranyl diphosphate synthase clone Mp13.18

( i x ) FEATURE:
        ( A ) NAME/KEY: CDS
        ( B ) LOCATION: 6..944

( x i ) SEQUENCE DESCRIPTION: SEQ ID NO:1:

```
TCAAA ATG GCC ATT AAT CTC TCC CAT ATC AAC TCC AAA ACA TGT TTC              4 7
      Met Ala Ile Asn Leu Ser His Ile Asn Ser Lys Thr Cys Phe
      1               5                   10

CCT CTC AAA ACA AGA TCT GAT CTC AGC CGT TCT TCT TCC GCG CGT TGC            9 5
```

| | | | | | | | | | | | | | | | | |
|---|---|---|---|---|---|---|---|---|---|---|---|---|---|---|---|---|
| | Pro 15 | Leu | Lys | Thr | Arg | Ser 20 | Asp | Leu | Ser | Arg | Ser 25 | Ser | Ser | Ala | Arg | Cys 30 |
| ATG Met | CCA Pro | ACT Thr | GCC Ala | GCC Ala 35 | GCT Ala | GCC Ala | GCC Ala | TTC Phe | CCC Pro 40 | ACT Thr | ATC Ile | GCC Ala | ACC Thr | GCC Ala 45 | GCC Ala | 143 |
| CAA Gln | AGT Ser | CAG Gln | CCG Pro 50 | TAC Tyr | TGG Trp | GCC Ala | GCC Ala | ATC Ile 55 | GAG Glu | GCC Ala | GAC Asp | ATA Ile | GAG Glu 60 | AGA Arg | TAC Tyr | 191 |
| CTG Leu | AAG Lys | AAA Lys 65 | TCC Ser | ATC Ile | ACA Thr | ATA Ile | AGG Arg 70 | CCG Pro | CCG Pro | GAG Glu | ACA Thr | GTT Val 75 | TTC Phe | GGG Gly | CCC Pro | 239 |
| ATG Met | CAC His 80 | CAC His | CTC Leu | ACC Thr | TTC Phe | GCC Ala 85 | GCC Ala | CCA Pro | GCC Ala | ACC Thr | GCC Ala 90 | GCC Ala | TCC Ser | ACC Thr | CTA Leu | 287 |
| TGC Cys 95 | TTG Leu | GCG Ala | GCG Ala | TGC Cys | GAG Glu 100 | CTC Leu | GTC Val | GGC Gly | GGC Gly | GAC Asp 105 | CGA Arg | AGC Ser | CAA Gln | GCC Ala | ATG Met 110 | 335 |
| GCA Ala | GCC Ala | GCG Ala | GCG Ala | GCG Ala 115 | ATC Ile | CAT His | CTC Leu | GTG Val | CAC His 120 | GCG Ala | GCA Ala | GCC Ala | TAC Tyr | GTC Val 125 | CAC His | 383 |
| GAG Glu | CAC His | CTC Leu | CCT Pro 130 | CTA Leu | ACC Thr | GAC Asp | GGG Gly | TCG Ser 135 | AGG Arg | CCC Pro | GTA Val | TCC Ser | AAG Lys 140 | CCC Pro | GCA Ala | 431 |
| ATC Ile | CAG Gln | CAC His 145 | AAG Lys | TAC Tyr | GGC Gly | CCG Pro | AAC Asn 150 | GTC Val | GAG Glu | CTC Leu | CTC Leu | ACC Thr 155 | GGA Gly | GAC Asp | GGG Gly | 479 |
| ATT Ile | GTC Val 160 | CCG Pro | TTC Phe | GGG Gly | TTT Phe | GAG Glu 165 | TTG Leu | CTG Leu | GCC Ala | GGG Gly | TCA Ser 170 | GTG Val | GAC Asp | CCG Pro | GCC Ala | 527 |
| CGA Arg 175 | ACA Thr | GAC Asp | GAC Asp | CCG Pro 180 | GAT Asp | AGG Arg | ATT Ile | CTG Leu | AGA Arg 185 | GTT Val | ATA Ile | ATA Ile | GAG Glu | ATC Ile 190 | AGT Ser | 575 |
| CGG Arg | GCC Ala | GGC Gly | GGG Gly | CCG Pro 195 | GAG Glu | GGA Gly | ATG Met | ATA Ile | AGC Ser 200 | GGG Gly | CTG Leu | CAT His | AGG Arg | GAA Glu 205 | GAA Glu | 623 |
| GAA Glu | ATT Ile | GTT Val | GAT Asp 210 | GGA Gly | AAT Asn | ACG Thr | AGT Ser | TTA Leu 215 | GAC Asp | TTC Phe | ATT Ile | GAA Glu | TAT Tyr 220 | GTG Val | TGC Cys | 671 |
| AAG Lys | AAA Lys | AAA Lys 225 | TAC Tyr | GGC Gly | GAG Glu | ATG Met | CAT His 230 | GCT Ala | TGC Cys | GGC Gly | GCG Ala | GCT Ala 235 | TGT Cys | GGA Gly | GCC Ala | 719 |
| ATA Ile | TTG Leu 240 | GGC Gly | GGC Gly | GCA Ala | GCC Ala | GAG Glu 245 | GAG Glu | GAG Glu | ATT Ile | CAG Gln | AAG Lys 250 | CTG Leu | AGG Arg | AAT Asn | TTC Phe | 767 |
| GGG Gly 255 | CTT Leu | TAT Tyr | CAA Gln | GGA Gly | ACT Thr 260 | CTC Leu | AGA Arg | GGA Gly | ATG Met | ATG Met 265 | GAA Glu | ATG Met | AAA Lys | AAT Asn | TCT Ser 270 | 815 |
| CAT His | CAA Gln | TTA Leu | ATT Ile | GAT Asp 275 | GAG Glu | AAT Asn | ATA Ile | ATT Ile | GGA Gly 280 | AAA Lys | TTG Leu | AAA Lys | GAA Glu | TTG Leu 285 | GCT Ala | 863 |
| CTC Leu | GAG Glu | GAG Glu | TTG Leu | GGA Gly 290 | GGC Gly | TTC Phe | CAC His | GGG Gly | AAG Lys 295 | AAC Asn | GCT Ala | GAG Glu | CTG Leu | ATG Met 300 | TCG Ser | 911 |
| AGC Ser | CTT Leu | GTA Val 305 | GCC Ala | GAG Glu | CCG Pro | AGC Ser | CTT Leu 310 | TAC Tyr | GCG Ala | GCT Ala | TAGAGCTATT | CGGATCCTTC | | | | 964 |
| ATTGCATTTT | CATGCGACAT | CTTCATATTC | ATATTGCATA | ATATTTTTA | AGCCAGTTAT | | | | | | | | | | | 1024 |
| TTTTTTATTA | TGAATTTTTT | TAACTGTTAT | TGATTTCGAA | AATACTGACA | ATCATCTAAA | | | | | | | | | | | 1084 |
| ATAAAGTAAA | TATAGTAAGG | ATGAAAAAAA | AAAAAAAAA | AAAAAA | | | | | | | | | | | | 1131 |

( 2 ) INFORMATION FOR SEQ ID NO:2:

( i ) SEQUENCE CHARACTERISTICS:
        ( A ) LENGTH: 313 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Ala Ile Asn Leu Ser His Ile Asn Ser Lys Thr Cys Phe Pro Leu
 1               5                  10                  15
Lys Thr Arg Ser Asp Leu Ser Arg Ser Ser Ala Arg Cys Met Pro
            20                  25                  30
Thr Ala Ala Ala Ala Ala Phe Pro Thr Ile Ala Thr Ala Ala Gln Ser
            35                  40                  45
Gln Pro Tyr Trp Ala Ala Ile Glu Ala Asp Ile Glu Arg Tyr Leu Lys
        50                  55                  60
Lys Ser Ile Thr Ile Arg Pro Pro Glu Thr Val Phe Gly Pro Met His
 65                  70                  75                  80
His Leu Thr Phe Ala Ala Pro Ala Thr Ala Ala Ser Thr Leu Cys Leu
                85                  90                  95
Ala Ala Cys Glu Leu Val Gly Gly Asp Arg Ser Gln Ala Met Ala Ala
            100                 105                 110
Ala Ala Ala Ile His Leu Val His Ala Ala Ala Tyr Val His Glu His
            115                 120                 125
Leu Pro Leu Thr Asp Gly Ser Arg Pro Val Ser Lys Pro Ala Ile Gln
    130                 135                 140
His Lys Tyr Gly Pro Asn Val Glu Leu Leu Thr Gly Asp Gly Ile Val
145                 150                 155                 160
Pro Phe Gly Phe Glu Leu Leu Ala Gly Ser Val Asp Pro Ala Arg Thr
                165                 170                 175
Asp Asp Pro Asp Arg Ile Leu Arg Val Ile Ile Glu Ile Ser Arg Ala
            180                 185                 190
Gly Gly Pro Glu Gly Met Ile Ser Gly Leu His Arg Glu Glu Glu Ile
            195                 200                 205
Val Asp Gly Asn Thr Ser Leu Asp Phe Ile Glu Tyr Val Cys Lys Lys
    210                 215                 220
Lys Tyr Gly Glu Met His Ala Cys Gly Ala Ala Cys Gly Ala Ile Leu
225                 230                 235                 240
Gly Gly Ala Ala Glu Glu Glu Ile Gln Lys Leu Arg Asn Phe Gly Leu
                245                 250                 255
Tyr Gln Gly Thr Leu Arg Gly Met Met Glu Met Lys Asn Ser His Gln
            260                 265                 270
Leu Ile Asp Glu Asn Ile Ile Gly Lys Leu Lys Glu Leu Ala Leu Glu
            275                 280                 285
Glu Leu Gly Gly Phe His Gly Lys Asn Ala Glu Leu Met Ser Ser Leu
    290                 295                 300
Val Ala Glu Pro Ser Leu Tyr Ala Ala
305                 310
```

( 2 ) INFORMATION FOR SEQ ID NO:3:

( i ) SEQUENCE CHARACTERISTICS:
        ( A ) LENGTH: 9 amino acids
        ( B ) TYPE: amino acid
        ( C ) STRANDEDNESS: Not Relevant ( D ) TOPOLOGY: Not Relevant ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
    ( A ) ORGANISM: Mentha spicata ( x i ) SEQUENCE DESCRIPTION: SEQ ID NO:3:

```
Phe Gly Leu Tyr Gln Gly Thr Leu Arg
1               5
```

( 2 ) INFORMATION FOR SEQ ID NO:4:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION:"Oligonucleotide PCR primer pMp13F"

( i i i ) HYPOTHETICAL: NO ( i v ) ANTI-SENSE: NO ( v i ) ORIGINAL SOURCE:
    ( A ) ORGANISM: Mentha piperita ( x i ) SEQUENCE DESCRIPTION: SEQ ID NO:4:

TTCCCTCTCA AAACAAGATC AG    22

( 2 ) INFORMATION FOR SEQ ID NO:5:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: "Oligonucleotide PCR primer pMp 13R"

( i i i ) HYPOTHETICAL: NO ( i v ) ANTI-SENSE: NO ( v i ) ORIGINAL SOURCE:
    ( A ) ORGANISM: Mentha piperita ( x i ) SEQUENCE DESCRIPTION: SEQ ID NO:5:

TACGGCTGAT TTTGGGCGG    19

( 2 ) INFORMATION FOR SEQ ID NO:6:

( i ) SEQUENCE CHARACTERISTICS:
    ( A ) LENGTH: 113 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: NO (v i) ORIGINAL SOURCE:
 (A) ORGANISM: Mentha piperita (x i) SEQUENCE DESCRIPTION: SEQ ID NO:6:

```
TTCCCTCTCA  AAACAAGATC  AGATCTCAGC  CGTTCTCCTT  CAGCACGTTG  CATGCCCACT    60
GCCGTCGCTG  CCGTCTTGCC  CACTCTCGCC  ACCGCCGCCC  AAAATCAGCC  GTA          113
```

(2) INFORMATION FOR SEQ ID NO:7:

(i) SEQUENCE CHARACTERISTICS:
  (A) LENGTH: 8 amino acids
  (B) TYPE: amino acid
  (C) STRANDEDNESS: Not Relevant
  (D) TOPOLOGY: Not Relevant (i i) MOLECULE TYPE: peptide (i i i) HYPOTHETICAL: NO (i v) ANTI-SENSE: NO (v) FRAGMENT TYPE: internal (v i) ORIGINAL SOURCE:
  (A) ORGANISM: Mentha spicata (x i) SEQUENCE DESCRIPTION: SEQ ID NO:7:

```
Arg  Val  Ile  Ile  Glu  Ile  Ser  Arg
1                  5
```